(12) United States Patent
Kurochkin et al.

(10) Patent No.: US 7,605,005 B2
(45) Date of Patent: Oct. 20, 2009

(54) METHOD OF SCREENING FOR AGENTS THAT MODULATE TYSND1 LEVEL OR ACTIVITY IN A CELL.

(75) Inventors: Igor Kurochkin, Yokohama (JP); Christian Schoenbach, Yokohama (JP); Yasushi Okazaki, Hidaka (JP)

(73) Assignees: Riken, Wako-shi (JP); Saitama Medical University, Iruma-gun (JP)

( * ) Notice: Subject to any disclaimer, the term of this patent is extended or adjusted under 35 U.S.C. 154(b) by 0 days.

(21) Appl. No.: 12/000,158

(22) Filed: Dec. 10, 2007

(65) Prior Publication Data
US 2008/0160023 A1 Jul. 3, 2008

Related U.S. Application Data

(63) Continuation of application No. PCT/JP2006/312085, filed on Jun. 9, 2006.

(30) Foreign Application Priority Data
Jun. 9, 2005 (JP) .............................. 2005-169380

(51) Int. Cl.
*G01N 33/68* (2006.01)
*C07K 16/40* (2006.01)
(52) U.S. Cl. ...................... 436/519; 435/7.21
(58) Field of Classification Search ........................ None
See application file for complete search history.

(56) References Cited

OTHER PUBLICATIONS

Keen Henry L. et al, "Gene expression profiling of potential PPARgamma target genes in mouse aorta," Physiological Genomics, 18(17), 2004, 33-42, XP002404515 ISSN: 1094-8341 cited in the application table 6.
Beier K. et al., "Selective Induction of Peroxisomal Enzymes by the Hypolipidemic Drug Bezafibrate Detection of Modulations by Automatic Image Analysis in Conjunction With Immunoelectron Microscopy and Immunoblotting," European Journal of Cell Biology, 46(3), 1988, 383-393, XP009073995 cited in the application abstract.
Kurochkin I.V. et al., "In Silico Prediction of Peroxisomal Proteins in Mouse," Genome Informatics, 14, 2003, 539-540, XP002404518 Retrieved from the Internet: <URL:http>://www.jsbi.org/journal/GIW03/GIWO3p068.pdf> cited in the application.
Kurochikin Igor V. et al., "Sequence-based discovery of the human and rodent peroxisomal proteome," Applied Bioinformatics. 4(2), 2005, 93-104, XP001247925 ISSN: 1175-5636 cited in the application.
Kurochkin I.V. et al, "Identification of Potential Peroxisomal Proteins in Mouse," Genome Research, 15, 2003, p. 1560, XP002404517 Retrieved from the Internet: URL:http://www.genome.org/cgi/reprint/13/6b/1560> cited in the application.
Database EMBL Feb. 8, 2001, "Mus musculus adult male liver cDNA, Riken full-length enriched library, done: 1300019N10 product hypothetical protein, full insert sequence," XP002404522 retrieved from EBI accession No. EM-PRO: AK005069 Database accession No. AK005069 & Carninci P et al: "High-Efficiency Full-Length CDNA Cloning" Methods in Enzymology, Academic Press Inc, San Diego, CA, US, vol. 303, 1999, pp. 19-44, XP001022979 ISSN: 0076-6879.
Subramani S. et al, "Import of peroxisomal matrix and membrane proteins," Annual Review of Biochemistry, 69, 2000, 399-418, XP002404519 ISSN: 0066-4154 cited in the application.
Titorenko V. I. et al, "Dynamics of peroxisome assembly and function," Trends in Cell Biology, Elsevier Science LTD, XX, 11(1), Jan. 2001, 22-29, XP002349975 ISSN: 0962-8924.
Gould S. J. et al., "Peroxisome biogenesis disorders—Genetics and cell biology," Trends in Genetics, Elsevier, Amsterdam, NL, 16(8), Aug. 2000, 340-345, XP004215200 ISSN: 0168-9525 cited in the application.
Kaiser E. et al., "Clinical Biochemistry of Peroxisomal Disorders," Clinica Chemica Acta, 173(1) 1988, 57-80, XP002404520 & Selection of Papers on Progress in Clinical Enzymology Presented at the 12th International Symposium ISSN: 0009-8981.
Purdue P. E. et al. "Peroxisome biogenesis," Annu Rev Cell Dev Biol. 2001;17:701-752 and Table of Contents (2 pages).
Olivier L. M. et al., "Identification of peroxisomal targeting signals in cholesterol biosynthetic enzymes," AA-CoA thiolase, hmg-coa synthase, MPPD, and FPP synthase, J Lipid Res., 2000; 41(12):1921-1935.
Osumi, T. et al., "Amino-terminal presequence of the precursor of peroxisomal 3-ketoacyl-CoA thiolase is a cleavable signal peptide for peroxisomal targeting," Biochem Biophys Res Commun. Dec. 31, 1991;181(3): 947-954.
Swinkels B. W. et al., "A novel, cleavable peroxisomal targeting signal at the amino-terminus of the rat 3-ketoacyl-CoA thiolase," EMBO J., 1991; 10(11): 3255-3262.
Tsukamoto T. et al. "Characterization of the signal peptide at the amino terminus of the rat peroxisomal 3-ketoacyl-CoA thiolase precursor," J Biol Chem., Feb. 25, 1994; 269(8): 6001-6010.
Hettema E. H. et al. "Import of proteins into peroxisomes,"Biochim Biophys Acta., Aug. 12, 1999; 1451(1): 17-34.
Titorenko V. I. et al., "The life cycle of the peroxisome," Nat Rev Mol Cell Biol., May 2001; 2(5): 357-368 and correction page.
Titorenko V. I. et al., "The peroxisome: orchestrating important developmental decisions from inside the cell," J Cell Biol., Mar. 1, 2004; 164(5): 641-645.
Cohen G. B. et al., "The human thioesterase II protein binds to a site on HIV-1 Nef critical for CD4 down-regulation," J Biol Chem., Jul. 28, 2000 ;275(30): 23097-23105.

(Continued)

*Primary Examiner*—Lorraine Spector
*Assistant Examiner*—Elly-Gerald Stoica
(74) *Attorney, Agent, or Firm*—Edwards Angell Palmer & Dodge LLP

(57) ABSTRACT

The invention relates to a pharmaceutical composition for treating or diagnosing a disorder associated with production of peroxisome in a cell, comprising a polypeptide which has cysteine protease activity and directly processes peroxisomal enzymes targeted by PTS1 or PTS2 signals. Preferably, the polypeptide is encoded by Tysnd1.

6 Claims, 11 Drawing Sheets
(1 of 11 Drawing Sheet(s) Filed in Color)

OTHER PUBLICATIONS

Gavva N. R. et al., "NAPP2, a peroxisomal membrane protein, is also a transcriptional corepressor," Genomics., Mar. 2002; 79(3): 423-431.

I. J. van der Klei et al., "Yeast peroxisomes: function and biogenesis of a versatile cell organelle," Trends Microbiol., Dec. 1997; 5(12): 502-509.

Veenhuis M. et al., "Peroxisome assembly in yeast," Microsc Res Tech., Jun. 2003, 1;61(2):139-150.

Olsen L. J. et al., "The surprising complexity of peroxisome biogenesis," Plant Mol Biol., Sep. 1998; 38(1-2): 163-189.

Hannaert V. et al., "Structure, function, and biogenesis of glycosomes in kinetoplastida," J Bioenerg Biomembr. Apr. 1994; 26(2): 205-212.

Moyersoen J. et al. "Biogenesis of peroxisomes and glycosomes: trypanosomatid glycosome assembly is a promising new drug target," FEMS Microbial Rev., 2004; 28(5): 603-643.

M. van de Kamp et al., "Compartmentalization and transport in beta-lactam antibiotic biosynthesis by filamentous fungi," Antonie Van Leeuwenhoek., Jan.-Feb. 1999; 75(1-2): 41-78.

Kikuchi M. et al., "Proteomic analysis of rat liver peroxisome: presence of peroxisome-specific isozyme of Lon protease," J Biol. Chem., Jan. 2004, 279(1): 421-428.

Jansen G. A. et al., "Molecular basis of Refsum disease: sequence variations in phytanoyl-CoA hydroxylase (PHYH) and the PTS2 receptor (PEX7)," Hum Mutat. Mar. 2004; 23(3): 209-218.

Sacksteder K. A. et al., "The genetics of peroxisome biogenesis," Annu Rev Genet 2000; 34: 623-652 & Table of Contents (2 pages).

Titorenko V. I. et al., "Pex20p of the yeast Yarrowia lipolytica is required for the oligomerization of thiolase in the cytosol and for its targeting to the peroxisome," J Cell Biol. Jul. 27, 1998; 142(2):403-420.

Glover J. R. et al., "Saccharomyces cerevisiae peroxisomal thiolase is imported as a dimer," Proc Nail Acad Sci U S A., Oct. 1994; 91: 10541-10545.

Leiper J. M. et al., "Inhibition of alanine: Glyoxylate aminotransferase 1 dimerization is a prerequisite for its peroxisome-to-mitochondrion mistargeting in primary hyperoxaluria type 1," J Cell Biol. Nov. 1996; 135(4): 939-951.

Bellion E. et al., "Proton ionophores prevent assembly of a peroxisomal protein," Cell. Jan. 16, 1987; 48(1): 165-173.

Waterham H. R. et al., "Peroxisomal targeting, import, and assembly of alcohol oxidase in Pichia pastoris," J Cell Biol., Dec. 15, 1997; 139(6); 1419-1431.

Marzioch M. et al., "PAS7 encodes a novel yeast member of the WD-40 protein family essential for import of 3-oxoacyl-CoA thiolase, a PTS2-containing protein, into peroxisomes," EMBO J. Oct. 17, 1994; 13(2); 4908-4918.

Albertini M. et al., "Pex14p, a peroxisomal membrane protein binding both receptors of the two PTS-dependent import pathways," Cell. Apr. 4, 1997; 89; 83-92.

Elgersma Y. et al., "A mobile PTS2 receptor for peroxisomal protein import in Pichia pastoris," J Cell Biol., Feb. 23, 1998, 140(4); 807-820.

Szilard R. K. et al., "Pay32p of the yeast Yarrowia lipolytica is an intraperoxisomal component of the matrix protein translocation machinery," J Cell Biol., Dec. 1995; 131(6); 1453-1469.

Zhang J. W. et al., "PEB1 (PAS7) in Saccharomyces cerevisiae encodes a hydrophilic, intra-peroxisomal protein that is a member of the WD repeat family and is essential for the import of thiolase into peroxisomes," J Cell Biol. Apr. 1995; 129(1): 65-80.

Morita M. et al., "Insulin-degrading enzyme exists inside of rat liver peroxisomes and degrades oxidized proteins," Cell Struct Funct. Oct. 2000; 25(5): 309-315.

Kawai J, et al., "Functional annotation of a full-length mouse cDNA collection," Riken Genome Exploration Research Group Phase II Team and the Fantom Consortium, Nature., Feb. 8, 2001; 409(6821):685-690.

Okazaki Y. et al., "Analysis of the mouse transcriptome based on functional annotation of 60,770 full-length cDNAs," Fantom Consortium; Riken Genome Exploration Research Group Phase, I & II Team., Nature., Dec. 5, 2002; 420(6915):563-573.

Van Veldhoven P.P. et al., "Iodixanol (Optiprep), an improved density gradient medium for the iso-osmotic isolation of rat liver peroxisomes," Anal Biochem., 1996; 237(1): 17-23.

McClelland G.B. et al. "Peroxisomal membrane monocarboxylate transporters: evidence for a redox shuttle system?" Biochem Biophys Res Commun. 2003; 304(1): 130-135.

Antonenkov V.D. et al., "The behavior of peroxisomes in vitro: mammalian peroxisomes are osmotically sensitive particles," Am J Physiol Cell Physiol., 2004; 287(6): C1623-C1635.

Johansson L.H. et al., "A spectrophotometric method for determination of catalase activity in small tissue samples," Anal Biochem., 1988; 174(1): 331-336.

Pennington RJ. "Biochemistry of dystrophic muscle," Mitochondrial succinate-tetrazolium reductase and adenosine triphosphatase, Biochem J. Sep. 1961; 80: 649-654.

Duckworth, W.C. et al., "Insulin degradation: progress and potential," Endocr Rev., 1998; 19(5): 608-624.

Kurochkin I.V., "Insulin-degrading enzyme: embarking on amyloid destruction," Trends Biochem Sci., Jul. 2001; 26(7): 421-425.

Gakh O. et al., "Mitochondrial processing peptidases," Biochim Biophys Acta., 2002; 1592(1): 63-77.

Dammai V. et al., "The human peroxisomal targeting signal receptor, Pex5p, is translocated into the peroxisomal matrix and recycled to the cytosol," Cell., Apr. 20, 2001; 105(2):187-196.

Nair DM et al., "Pex7p translocates in and out of peroxisomes in Saccharomyces cerevisiae," J Cell Biol., Nov. 22, 2004; 167(4): 599-604.

Tsukamoto T. et al, "Isolation and characterization of Chinese hamster ovary cell mutants defective in assembly of peroxisomes," I Cell Biol., Mar. 1990;110(3): 651-660.

Miyazawa S. et al., "Complete nucleotide sequence of cDNA and predicted amino acid sequence of rat acyl-CoA oxidase," J Biol Chem., Jun. 15, 1987; 262(17): 8131-8137.

Miyazawa S. et al., "Peroxisome targeting signal of rat liver acyl-coenzyme a oxidase resides at the carboxy terminus," Mol Cell Biol., Jan. 1989; 9(1): 83-91.

Wirtz K.W., "Phospholipid transfer proteins revisited," Biochem J., 1997; 324, 353-360.

Seedorf U. et al., "Sterol carrier protein-2," Biochim Biophys Acta. 2000; 1486(1): 45-54.

Otera H. et al., "Biogenesis of nonspecific lipid transfer protein and sterol carrier protein x: studies using peroxisome assembly-defective pex cell mutants," J Biol Chem., Jan. 26, 2001; 276(4): 2858-2864.

Mukherji M. et al., "Utilization of sterol carrier protein-2 by phytanoyl-CoA 2-hydroxylase in the peroxisomal alpha oxidation of phytanic acid," Chem Biol. May 2002; 9(5): 597-605.

Ferdinandusse S. et al., "Identification of the peroxisomal beta-oxidation enzymes involved in the degradation of long-chain dicarboxylic acids," J Lipid Res. Jun. 2004; 45(6):1104-1111.

Huyghe S. et al., "Peroxisomal multifunctional protein 2 is essential for lipid homeostasis in Sertoli cells and male fertility in mice," Endocrinology, 2006; [Epub ahead of print as doi:10.1210/en.2005-1571; 2228-2236.

Jiang L. L., et al., "Physiological role of D-3-hydroxyacyl-CoA dehydratase/D-3-hydroxyacyl-CoA dehydrogenase bifunctional protein," J Biochem (Tokyo). 1997; 121(3): 506-513.

Seedorf U. et al., "Sterol carrier protein X is peroxisomal 3-oxoacyl coenzyme A thiolase with intrinsic sterol carrier and lipid transfer activity," J Biol Chem., Aug. 19, 1994; 269(33): 21277-21283.

Antonenkov V.D. et al., "Substrate specificities of 3-oxoacyl-CoA thiolase A and sterol carrier protein 2/3-oxoacyl-CoA thiolase purified from normal rat liver peroxisomes. Sterol carrier protein 2/3-oxoacyl-CoA thiolase is involved in the metabolism of 2-methyl-branched fatty acids and bile acid intermediates," J Biol Chem. Oct. 10, 1997; 272(41)26023-26031.

Wouters F.S. et al., "FRET microscopy demonstrates molecular association of non-specific lipid transfer protein (nsL-TP) with fatty acid oxidation enzymes in peroxisomes," EMBO J., 1998; 17(24): 7179-7189.

Cal S. et al., "Polyserase-I, a human polyprotease with the ability to generate independent serine protease domains from a single translation product," Proc Nail Acad Sci U S A. Aug. 5, 2003; 100(16): 9185-9190.

Cal S. et al., "Human polyserase-2, a novel enzyme with three tandem serine protease domains in a single polypeptide chain," J Biol Chem. Jan. 21, 2005; 280(3):1953-1961.

Sandy P. et al., "Mammalian RNAi: a practical guide," Biotechniques. Aug. 2005; 39(2):215-224.

Biermann J. et al., "In vitro processing of the human alkyl-dihydroxyacetonephosphate synthase precursor," Arch Biochem Biophys. Aug. 1, 1999; 368(1):139-146.

Dyck J.R.B. et al., "Malonyl coenzyme a decarboxylase inhibition protects the ischemic heart by inhibiting fatty acid oxidation and stimulating glucose oxidation," Circ Res. 2004; 94(9):e78-84.

Lopaschuk G.D., "Inhibiting fatty acid oxidation as a novel therapeutic approach to treating, ischaemic heart disease," Cardiovasc J S Afr. Jul. 2004; 15(4 Suppl 1):S1.

Murase, T. et al., "Dietary diacylglycerol suppresses high fat and high sucrose diet-induced body fat accumulation in C57BL/6J mice," J. Lipid Res. 42, 2001, 372-378.

Kim, S. et al., "Hepatic gene expression profiles in a long-term high-fat diet-induced obesity mouse model," Gene. Sep. 29, 2004; 340(1):99-109.

Raychaudhury B. et al., "Peroxisomal function is altered during leishmania infection," Med Sci Monit. Apr. 2003; 9(4):BR165-169.

Written Opinion of the International Search Authority (WOSA), issued in PCT/JP2006/312085.

International Preliminary Report on Patentability Chapter II (IPRP2) dated Oct. 24, 2007, issued in PCT/JP2006/312085.

International Search Report dated Nov. 20, 2006, issued in PCT/JP2006/312085.

UCSC Genome browser; mouse Tysndl http://genome.ucsc.edu/cgi-bin/hgTracks?db=mm5&position=chr10:61457382-614646348zhgsid=39784308; Release/Date—Build 33 assembly of the mouse genome (mm5, May 2004).

UCSC Genome browser; human TYSND1 http://genome.ucsc.edu/cgi-bin/hgTracks?db=hg17&position=chr10:71568974-71575956&hgsid=39784308; Release/Date—Build 35 finished human genome assembly (hg17, May 2004).

Gene Entrez mouse Tysndl http://www.ncbi.nlm.nih.gov/entrez/query.fcgi?db=gene&cmd=Retrieve&dopt=Graphics&list_uids=71767; Release/Date—Jan. 2005 (Entrez Gene: gene-centered information at NCBI. Magiott D, Osteil J, Pruitt KD, Tatusova T. Nucleic Acids Res. Jan. 1, 2005; 33 (Database issue): D54-8.).

Gene Entrez human TYSND1 <http://www.ncbi.nlm.nih.gov/entrez/query.fcgi?db=gene&cmd=Retrieve&dopt=Graphics&list_uids=219743; Release/Date—Jan. 2005(Entrez Gene: gene-centered information at NCBI. Magiott D, Ostell J, Pruitt KD. Tatusova T. Nucleic Acids Res. Jan. 1, 2005; 33 (Datatbase Issue): D54-8.

Swissprot/TrEMBL mouse Tysdn1 and human TYSND1: http://kr.expasy.org/cgi-bin/sprot-search-de?TYSDN1 or http://kr.expasy.org/cgibin/sprot-search-de?Tysnd1; Release—47 from May 2005: Comment: Note, in the meantime the URL is obsolete because Swissprot became part of Uniprot. The new URL is http://www.uniprot.org/uniprot/?query=Tysnd1=score or is Http://www.uniprot.org/uniprot/?query=TYSND1=score.

Interpro domain: Peptidase, tryspin-like sering and cysteine proteases accession No. http://www.ebi.ac.uk/interpro/ISpy?mode=sinqle&ac=[SwissProt/TrEMBLaccessionnumber]; Release/Date—10.0 from Apr. 26, 2005.

UCSC Genome browser; gene expression for mouse Tysndl and neighbors <http://genome.ucsc.edu/cgi-bin/hgNear?hgsid=39784308&org=Mouse&db=mm5>&near_search=AK005069&submit=Go%21&near.order=expGnfAtlas2&near.count=50; Release/Date—Build 33 assembly of the mouse genome (mm5, May 2004).

Mouse Gene Prediction Database; Search Results for 1300019N1ORik (XM_125636.1) and top 100 correlated genes. http://mgpd.med.utoronto.ca/profile.php?nameofgene=XM 125636.1; Release/Date—Release from Dec. 6, 2004.

UCSC Genome browser; gene expression for human TYSND1 and neighbors <http://genome.ucsc.edu/cgi-bin/hgNear?hgsid=73232388&org>=Hurnan&db=hg18&near_search=TYSNDI&submit=Go%21&near_order=expGnfAtlas2knear.count=50; Release/Date—Build 36.1 finished human genome assembly (hg18, Mar. 2006): Comment: in original submitted version to Riken (Mr Tsujigami)Build 35 finished human genome assembly (hg17, May 2004) was used. During correction and update of patent the in 2006 Build 36.1 hg 18, Mar. 2006 release was used.

InterPro domain view for mouse Tysnd1 http://www.ebi.ac.uk/interpro/ISpy?mode=single&ac=Q9DBA6; Release/Date —Release 10.0 from Apr. 26, 2005.

Salvesen. G.S, Nagase H. Inhibition of proteolytic enzymes. In Proteolytic Enzymes: A Practical Approach (eds. Beynon R and Bond JS) p. 110. Oxford University Press, 2001.

METHOD OF SCREENING FOR AGENTS THAT MODULATE TYSND1 LEVEL OR ACTIVITY IN A CELL.

CROSS-REFERENCE TO RELATED APPLICATION

This is a continuation of Application No. PCT/JP2006/312085, filed on Jun. 9, 2006.

BACKGROUND OF THE INVENTION

1. Field of the Invention

The present invention relates to nucleic acid sequences that encode polypeptides targeted to the peroxisome, wherein the polypeptides have protease activity and process peroxisomal enzymes. In a particular embodiment, the invention provides proof that the peroxisomal protease Tysnd1 is capable of processing PTS1- and PTS2-signal containing enzymes Acaa1, Acox1, Scp2, and Hsd17b4 involved in the peroxisomal β- and α-oxidation. The invention further relates to therapeutic, diagnostic and research methods for diagnosis, treatment, and prevention of disorders involving any one of these mammalian nucleic acids encoding peroxisomal proteases.

2. Description of the Related Art

Peroxisomes are organelles present in all eukaryotic organisms studied so far. Since peroxisomes lack DNA and protein synthesis capabilities, all peroxisomal proteins are synthesized in the cytosolic compartment and post-translationally sorted to the peroxisome [1-2]. Two distinct peroxisomal signal targeting sequences (PTS) and their variants, the C-terminal PTS1 and the N-terminal PTS2, have been defined. Almost all peroxisomal enzymes have the PTS1 signal [SA]-K-L which was subsequently expanded to [STAGQCN]-[KRH]-[LIVMAFY][3] and this PTS1 signal is recognized by the cytosolic soluble receptor Pex5p. Only a few peroxisomal proteins are targeted via the N-terminally located PTS2 motif [RK]-[LVI]-[X5]-[HQ]-[LAF][4-6]. A small number of peroxisomal matrix proteins that lack both PTS1 and PTS2 signals are targeted to the organelle by poorly defined internal PTSs [7].

The function of peroxisomes is extremely diverse and dependent on the cell type and external stimuli. In humans peroxisomes are involved in a variety of anabolic and catabolic pathways (e.g. cholesterol biosynthesis, fatty acid oxidation, purine metabolism, hydrogen peroxide detoxification, bile acid synthesis, plasmalogen synthesis, amino acid metabolism) [8-9], infectivity of human immunodeficiency virus and rotavirus [10] and certain developmental processes that are independent of the metabolic state [11]. In yeast, peroxisomes are essential for the metabolism of unusual carbon sources such as oleic acid, primary amines, purines, D-amino acids, and methanol [12-13]. In plants, peroxisomes are involved in photorespiration [14], in trypanosomes peroxisomes are involved in glycolysis [15-16], and in fungi they are involved in the synthesis of secondary metabolites, for example beta-lactam penicillins [17].

Mass spectrometry (MS), in combination with the rapid development of sequence databases has significantly enhanced the global characterization of the peroxisomal protein composition in model organisms. The MS-based methodology allowed the identification of 34 known and five putative peroxisomal proteins from rat liver [18] Kikuchi et al 2004). Several genes are involved in the production of peroxisomes in a cell, which is also termed peroxisomal biogenesis. So-called PEX genes encoding peroxins, have been cloned by the functional complementation of yeast mutant strains lacking functional peroxisomes [7]. Thirteen human PEX homologues have been identified through sequence database screening, of which 11 were shown to restore peroxisome biogenesis in cell lines of patients with peroxisomal disorders [19]. Defects in peroxisomal biogenesis contribute to several inherited human disorders, such as Refsum's disease [20], X-linked adrenoleukodystrophy (X-ALD), mevalonic aciduria [21] among other metabolic diseases.

The import of peroxisomal proteins does not seem to involve significant protein modifications [22]. Folded polypeptides and protein dimers can be imported into the peroxisomal matrix [23-24]. Alcohol oxidase monomers are imported into the matrix before the assembly of enzymatically active octamers [25-26], and alanine: glyoxylate aminotransferase 1 can be imported with equal efficiency as a dimer or monomer [24]. Two peroxisomal import models have been proposed. One model proposes that peroxisomal import receptors are shuttling between the cytosol and the peroxisome [27-29]. The other model suggests that peroxisomal receptors pull proteins into the peroxisome [30-31].

However little is known about the fate of proteins with regard to processing, activation, degradation and associated diseases thereof once they have entered the peroxisome. So far two proteases, insulin-degrading enzyme (IDE) [32] and a peroxisome-specific form of Lon protease [18], have been experimentally detected in peroxisomes. IDE may play a role in degradation of oxidized peroxisomal lysozymes while the novel LON protease might be involved in peroxisome biogenesis.

Kurochkin et al. [33-35] computationally identified in a search of 130629 putative translations of GenBank 139.0 rodent and primate mRNA sequences 29 novel peroxisome PTS1-targeted protein candidates. One of the candidates 1300019N10Rik, which is now called Tysnd1 or trypsin domain containing 1 (GenBank and GenPept accessions AK005069 and BAB23793) and its orthologs in rat (XM_345106 and XP_345107), and human (NM_173555 and NP_775826) are weakly similar to a protease-related protein derived from *Arabidopsis thaliana*. It also contains two protease-related domains, glutamyl endopeptidase I (IPR008256) and trypsin-like serine and cysteine proteases (IPR009003). The members of the glutamyl endopeptidase I family of proteases possess serine-type peptidase activity. Proteolytic enzymes that exploit serine in their catalytic activities are ubiquitous, being found in viruses, bacteria and eukaryotes. The peroxisome is likely to recruit a wide spectrum of proteases, each with a unique specificity, to achieve efficient breakdown of proteins in the organelle.

Tysnd1 is located on mouse chromosome 10. Its human ortholog maps in syntenic position to chromosome 10. Tysnd1 is expressed in adipose tissue, aorta, liver, kidney and lung (see Table 1). Co-expressed genes include Peci, Pex6, Pex16, which are known to encode peroxisome-targeted gene products. Other co-expressed genes (e.g. Fsp27 and Cas1) are associated with fat metabolism. The data derived from public gene expression resources (GNF U74A, GNF Atlas 2, Mouse Gene Prediction Database) suggest that Tysnd1 is involved in peroxisome-regulated fat metabolism.

TABLE 1

Tysnd1 gene structure, motifs, expression patterns

|  | Mouse Tysnd1 | Human TYSND1 |
|---|---|---|
| Chromosome and orientation | 10, +strand [36] | 10; −strand [37] |
| Position | 61, 457, 382-61, 464, 634 (NCBI 33 genome assembly) [36] | 71, 568, 974-71, 575, 956 (NCBI 35 genome assembly) [37] |
| Exon no | 4 [36] | 2-4 [37] |
| Neighboring gene | upstream: Sara1 downstream: Amid [36] | upstream: AMID downstream: SARA1 [37] |
| Transcript information | AK005069, AW121748, AW490206, BB224225 (GenBank) [38] | BC016840, BC030242, BC042629, BC047424 (GenBank) [39] |
| Protein information | BAB23793 568 aa (GenPept); Q9DBA6 568 aa (SwissProt/TrEBML) [38, 40] | AAH16840 435 aa, AAH30242 398 aa, AAH42629 399 aa (GenPept), Q96AR5 (SwissProt/TrEMBL) 435 aa, Q8IVQ3 399aa, Q5SQU1 398 aa, Q5SQT4 566 aa [39, 40] |
| InterPro motifs | Peptidase, trypsin-like serine and cysteine protease; positions 27-42, 187-294 and 308-531 of Q9DBA6 [41] | Peptidase, trypsin-like serine and cysteine potease; positions 54-162 and 222-398 of Q96AR5; 289-534 of Q5SQT4; 309-373 of Q5SQU1 [41] |
| Expression | Kidney, liver, lung, adipose tissue, aorta, brown fat [42, 43] | Testis, lung, liver, adipocytes, skin, thymus [44] |
| Co-expressed genes | Pex16, Pex6, Peci, Cas1, Fsp27, Amid, Scp2, Acaa1, and others [42, 43] | ACAT1, ADH5, COX10 homolog and others [44, 45] |

BRIEF SUMMARY OF THE INVENTION

Tysnd1 or trypsin domain-containing 1 was originally reported as hypothetical protein [46, 47]. Functional information on protein level that is available in public database (Gene Entrez [39], SwissProt/TrEMBL [40]) was computationally inferred and is based on protein motif and sequence homology searches. Here we describe for the first time the in vitro validation of Tysnd1 protein functions. The functions include 1) localization to the peroxisomes, 2) peroxisomal protease function, 3) proteolytic cleavage of PTS2-containing peroxisomal enzymes, 4) proteolytic cleavage of PTS1-containing peroxisomal enzymes and 5) the post-translational processing of the precursor Tysnd1 to mature Tysnd1. Functions 2)-4) were demonstrated with rat 3-ketoacyl-CoA thiolase B, peroxisomal precursor RGD1562373-predicted), rat acyl-Coenzyme A oxidase 1 (Acox1), mouse sterol carrier protein 2 (Scp2), and hydroxysteroid (17-beta) dehydrogenase 4 (Hsd17b4) as Tysnd1 substrates.

In one aspect, the invention provides a pharmaceutical composition for treating a disorder associated with production of and function of peroxisomes in a cell, comprising a polypeptide which has protease activity and processes a peroxisomal enzyme.

In a further aspect, the invention provides a method for treating a subject (e.g. a human patient) diagnosed with a disease or syndrome associated with the production and/or function of peroxisomes in a cell, comprising administering to said subject a polypeptide which has a protease activity and processes a peroxisomal enzyme.

Preferably, the polypeptide is encoded by Tysnd1. The peroxisome enzyme may be at least one selected from the group consisting of 3-oxoacyl-Coenzyme B thiolase (hereinafter called the "Acaa1"), acyl-Coenzyme A oxidase 1 (Acox1), palmitoyl sterol carrier protein 2 (Scp2), and hydroxysteroid (17-beta) dehydrogenase 4(Hsd17b4). The disease may be selected from the group consisting of Refsum's disease, X-linked adrenoleukodystrophy (X-ALD), mevalonic aciduria, male infertility among other metabolic diseases.

In another aspect, the invention provides a pharmaceutical composition for diagnosing a disorder associated with production and function of peroxisomes in a cell, comprising a polypeptide which has protease activity and processes a peroxisome enzyme.

Preferably, the polypeptide is encoded by Tysnd1. The peroxisome enzyme may be at least one selected from the group consisting of 3-oxoacyl-Coenzyme B thiolase (Acaa1), acyl-Coenzyme A oxidase 1 (Acox1), palmitoyl sterol carrier protein 2 (Scp2), and hydroxysteroid (17-beta) dehydrogenase 4 (Hsd17b4). The disease may be selected from the group consisting of Refsum's disease, X-linked adrenoleukodystrophy (X-ALD), mevalonic aciduria, male infertility among other metabolic diseases.

BRIEF DESCRIPTION OF THE SEVERAL VIEWS OF THE DRAWINGS

The file of this patent contains at least one drawing executed in color. Copies of this patent with color drawing(s) will be provided by the Patent and Trademark Office upon request and payment of the necessary fee.

The objects and features of the invention can be better understood with reference to the following detailed description and accompanying drawings.

FIG. 7B shows the protein content. Proteins from equal volumes of each fraction were separated by 12.5% SDS-PAGE and immunoblotted with an antibody against mouse Tysnd1 (FIG. 7C).

DETAILED DESCRIPTION OF THE INVENTION

Definition

Figure 1:
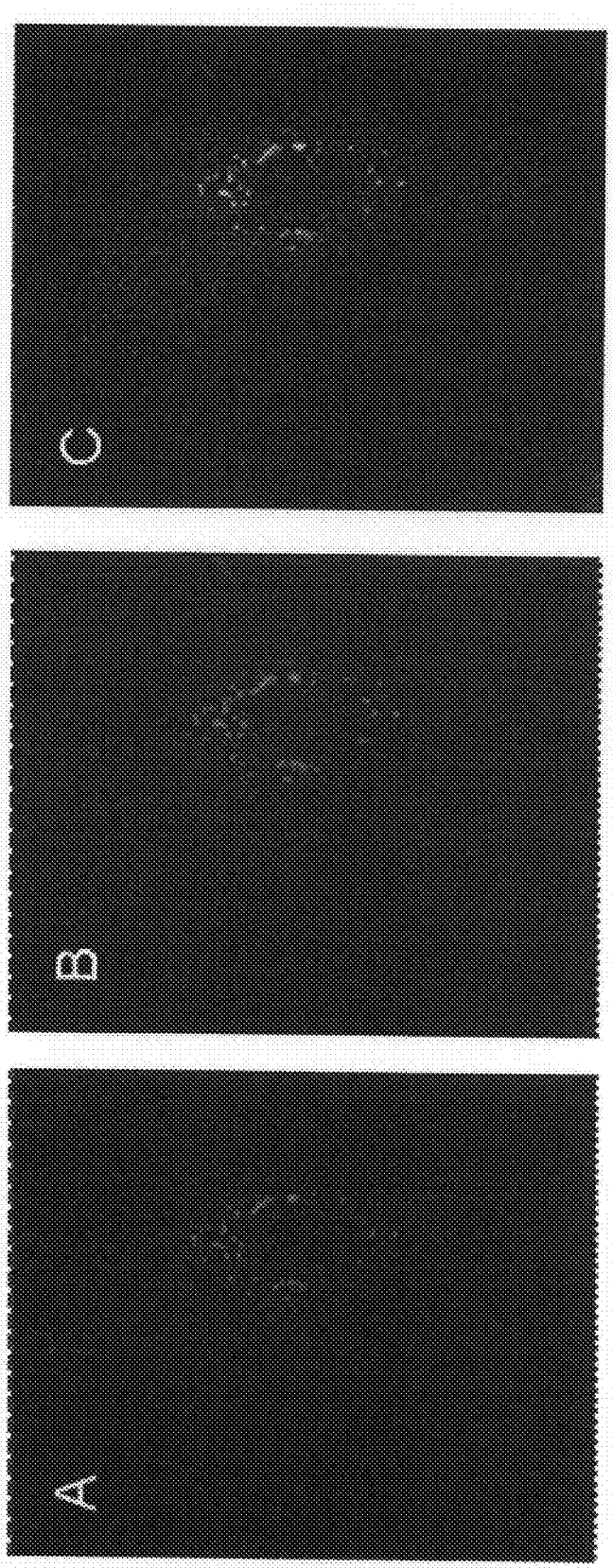
FIG. 1 shows fusion protein GFP-Tysnd1 localizes to peroxisomes. CHO-K1 cells were co-transfected with plasmids expressing fused GFP-Tysnd1 and DsRed2-Peroxi. Living cells were analyzed by fluorescence microscopy, and representative images for the GFP (A), DsRed (B) channels, and merged signals (C) are shown.

The practice of the present invention will employ, unless otherwise indicated, conventional techniques of molecular biology, which are within the skill of the art.

Such techniques are explained fully in the literature.

The following definitions are provided for specific terms which are used in the following written description.

As used herein, the term "peroxisome" refers to an enzyme-bearing, membrane bound vesicle found in eukaryotic cells. Peroxisome is sometime called microbody. Peroxisome serves to sequester such enzymes from the rest of the cell, organizing the cellular metabolism.

As used herein, the term "process" a polypeptide refers to cleavage (especially hydrolytic cleavage) of a synthesized polypeptide in a cell to form the mature protein or peptide. The polypeptide may be modified amino acid residues such as by addition of other group, folded into its active three-dimensional conformation, or targeted for degradation.

The term "Tysnd1" refers to a genomic DNA sequence which is located on chromosome 10 (mouse) and its gene products. Its human ortholog maps in syntenic position to chromosome 10. The characterization of Tysnd1 is shown in Table 1 above.

The present invention will now be described more fully hereinafter with reference to the accompanying figures, in which embodiments of the invention are shown.

Embodiments

Material and Methods

Primers used for construction of expression vectors Primers B1 and B2 are based on the Tysnd1 nucleotide sequence of GenBank accession AK005069. B1 and B2 were used for construction plasmid vector, pEGFP-Tysnd1.

B1 (forward) 5'-GGATCCATGGGGCGGCAATGGGGAC-3' (SEQ ID NO: 1) contains the BamHI site (GGATCC) and Tysnd1 sequence positions 59-77.

B2 (reverse) 5'-GGATCCTCAGAGCTTGCTCCGTGG-GAC-3' (SEQ ID NO: 2) contains the BamHI site (GGATCC) and Tysnd1 sequence positions 1745-1765.

Primers AX1 and AX2 are based on the rat Acox1 nucleotide sequence of GenBank accession BC085743

AX1 (forward)
5'-ACCATGGGC<u>TACCCTTACGACGTGCCTGAC TACGCC</u> AACCCCGACCTGCGCA AGGAGC-3' (SEQ ID NO: 3) contains a synthetic Kozak sequence (bold) surrounding the ATG start codon. The HA-tag peptide TyrAspVal ProAspTyrAla is encoded by the underlined sequence. Positions 37-58 of the primer correspond to Acox1 sequence positions 94 to 115 of BC085743.

AX2 (reverse) 5'-TCAAAGCTTGGACTG-CAGGGGCTTC-3' (SEQ ID NO: 4) contains Acox1 sequence positions 2052-2076. The stop codon was included.

Primers S5 and S2 are based on the mouse Scp2 nucleotide sequence of GenBank accession BC034613.

S5 (forward)
5'-ACCATGGGCTACCCT<u>TACGACGTGCCTGACTAC GCC</u> CCTTCTGTCGCTTTGA

A-3'
ATCTCC (SEQ ID NO: 5) contains a synthetic Kozak sequence (bold) surrounding the ATG start codon. The HA-tag peptide TyrAspVal ProAspTyrAla is encoded by the underlined sequence. Positions 37-59 of the primer correspond to Scp2 sequence positions 25-57.

S2 (reverse) 5'-CTCCTCACAGCTTAGCTTTGC-3' (SEQ ID NO: 6) corresponds to Scp2 sequence positions 1649-1669. The stop codon was included.

Primers Hsd17b4-Fwd and Hsd17b4-Rev are based on the mouse Hsd17b4 nucleotide sequence of GenBank accession AK004866.

Hsd17b4-Fwd (forward)
5'-ACCATGGGCTACCCT<u>TACGACGTGCCTGACTAC GCC</u>GCTTCGCCGCTGAGGT TCGAC-3'(SEQ ID NO: 17) contains a synthetic Kozak sequence (ACCATGG) surrounding the ATG start codon. The HA-tag peptide TyrAspVal ProAspTyrAla is encoded by the underlined sequence. Positions 37-57 of the primer correspond to Hsd17b4 sequence positions 155-175.

Hsd17b4-Rev (reverse) 5'-TCAGAGCTTGGCATAGTCTT-TAAGAAT-3' (SEQ ID NO: 18) corresponds to Hsd17b4-Rev sequence positions 2359-2333. The stop codon was included.

Primers for Flag-tagged Tysnd1 are based on the sequence of GenBank accession AK005069.

FN (forward)
5'-CCACCATGGACTACAAAGACGATGACGA-CAAGGGGCGGCAATGGGGAC-3' (SEQ ID NO: 7) includes the Kozak sequence (CCACCATGG), FLAG epitope (GACTACAAAGACGATGACGACAAG, SEQ ID NO: 8) and Tysnd1 sequence positions 62-77 (GGGCG-GCAATGGGGAC, SEQ ID NO: 9).

FC1 (forward) 5'-CCACCATGGGGCGGCAATGGGGAC-3' (SEQ ID NO: 10 includes the Kozak sequence (CCAC-CATGG) and Tysnd1 sequence positions 62-77 (GGGCG-GCAATGGGGAC, SEQ ID NO: 9).

FC2 (reverse)
5'-TCAGAGCTTGCTCCGTGGGACCT-TGTCGTCATCGTCTTTGTAGTCTTCGGAC

AGG
GGCCGCTGCAG-3' (SEQ ID NO: 11) includes Tysnd1 sequence positions 1724-1744, the FLAG epitope (CT-TGTCGTCATCGTCTTTGTAGTC, SEQ ID NO: 12 and six amino acids from the C-terminus of Tysnd1 (Val-ProArgSerLysLeu, SEQ ID NO: 13) corresponding to nucleotide sequence positions 1745-1765.

Cells and Transfections
COS-7 (Simian fibroblasts transformed by SV40), 293FT (a fast growing variant of human 293 cells expressing SV40 large T-antigen) and Chinese hamster ovary CHO-K1 cells were maintained in Dulbecco's modified Eagle's medium supplemented with 10% (v/v) fetal calf serum (Invitrogen) and transiently transfected using LipofectAMINE 2000 reagent (Invitrogen), according to the manufacturer's instructions.

Construction of Expression Vector for Green Fluorescent Protein (GFP) Fusion Protein
The DNA fragment encoding the full-length mouse Tysnd1 was amplified by PCR with the primer set B1 and B2 using the cloned cDNA 1300019N10 (GenBank accession AK005069) as a template. The PCR product was subcloned into pGEM-T Easy vector (Promega). After digestion with BamHI, the resulting fragment was inserted into the BamHI site of pEGFP-C1 (EGFP is enhanced GFP; BD Biosciences Clontech). The resulting vector was designated pEGFP-Tysnd1.

Expression of epitope-tagged rat peroxisomal 3-oxoacyl-Coenzyme B thiolase (Acaa1), rat acyl-Coenzyme A oxidase 1 (Acox1), mouse palmitoyl sterol carrier protein 2 (Scp2), and hydroxysteroid (17-beta) dehydrogenase 4 (Hsd17b4).

The following vectors were utilized: rat type-B pre-3-ketoacyl-CoA thiolase-HA (HA=hemagglutinin) in pcDNA3.1Zeo (a gift from Y. Fujiki, Kyushu University), pcDNA3.1/TOPO-HA-Acox1, pcDNA3.1/TOPO-HA-Scp2. HA tagging to the N-terminus of rat Acox1 was done with a PCR-based technique using a forward primer AX1 containing the HA epitope and a reverse primer AX2 containing a stop codon. Similarly, the HA-tag was introduced into Scp2 and Hsd17b4 by PCR using the primers S5 and S2 and Hsd17b4-Fwd and Hsd17b4-Rev, respectively. The amplified DNA products were cloned into pcDNA3.1/V5-His-TOPO (Invitrogen). All plasmid constructs were checked for orientation of the inserts and used for transfection.

Expression of Epitope-Tagged Tysnd1
For expression of mouse Tysnd1 in cultured cells, two vectors were constructed. pcDNA3.1/TOPO-FLAG-Tysnd1 contains a FLAG epitope at the N-terminus of Tysnd1. pcDNA3.1/TOPO-Tysnd1-FLAG contains a FLAG epitope at the C-terminus of Tysnd1. To make pcDNA3.1/TOPO-FLAG-Tysnd1, PCR amplification of the full-length Tysnd1 was performed with the forward primer FN1 containing the FLAG epitope and the reverse primer B2-containing a stop codon. To construct pcDNA3.1/TOPO-Tysnd1-FLAG, a FLAG epitope was introduced between amino acids 562 and 563, thereby preserving the native PTS1-containing C-terminus of Tysnd1. PCR amplification was performed with the forward primer FC1 and the reverse primer FC2. The latter contains in addition to the FLAG sequence the C-terminal Tysnd1 sequence encoding amino acids Val-Pro-Arg-Ser-Lys-Leu (position 563-568) plus a stop codon. The constructs were used for the transfection experiments as described above.

Localization of GFP Fusion Protein
CHO-K1 cells were plated onto glass cover slips and transiently transfected with expression vectors pEGFP-Tysnd1 and pDsRed2-Peroxi (variant 2 of red fluorescent protein from *Discosoma* sp), encoding peroxisome-targeted DsRed2 reporter protein (BD Biosciences Clontech). Live cell microscopy of EGFP fusion and DsRed2-Peroxi proteins was performed 48 h after transfection on a laser scanning confocal microscope TCS SP2 (Leica) using a 63× objective. An argon laser at 488 nm was used for excitation. The fluorescent signals emitted by GFP and DsRed2 were detected using a 535-nm band-pass filter and a 570-nm long pass filter, respectively.

Immunoblotting Analysis

Cells were transfected as described above. After 48 h, cells were lysed in buffer A (20 mM Tris-HCl, pH 7.5, 120 mM NaCl, 1% Triton X-100 supplemented with the Complete™ Protease inhibitor cocktail from Roche Diagnostics GmbH) and centrifuged at 12,000×g for 15 min. The supernatant fraction was separated by SDS-PAGE. Western blot analysis was performed using electrophoretically transferred samples on Hybond-P polyvinylidene difluoride membrane (Amersham Biosciences, Inc.) with the HA.11 monoclonal antibody (Covance) or anti-FLAG™ M2 antibody (Sigma) and a second antibody, sheep anti-mouse IgG antibody conjugated to horseradish peroxidase (Amersham Biosciences, Inc.). Antigen-antibody complexes were visualized with the ECL plus Western Blotting detection reagent (Amersham Biosciences, Inc.). The apparent molecular weight of protein bands was estimated by comparing with a mobility of pre-stained Precision Plus Protein™ Standards (Bio-Rad).

Purification of Peroxisomes

Peroxisomes were purified by a method based on the combination and modification of three previously described protocols [48-50]. Briefly, male Wistar rats (250-300 g) were fasted overnight. After the animals were killed by diethyl ether inhalation, the livers were perfused via the portal vein. Livers were finely minced with scissors in ice-cold homogenization buffer (0.16M sucrose, 12% (wt/vol) PEG 1500, 10 mM MOPS, pH 7.4, 1 mM EDTA, 1 mM EGTA, 1 mM DTT, 0.1% (vol/vol) ethanol) and homogenized in a Potter-Elvehjem homogenizer (Teflon on glass). The nuclei and heavy mitochondria were pelleted by centrifugation at 3,000×g in a fixed-angle rotor for 10 min at 4° C. The pellet was re-homogenized and the centrifugation repeated. The supernatants (post-nuclear fractions) were combined and centrifuged at 20,000×g for 20 min to produce a "light mitochondrial pellet". This pellet was resuspended in the homogenization buffer using a loose-fitting Dounce homogenizer. The volume was adjusted to 15 ml/10 g starting liver weight and mixed with an equal volume of gradient solution consisting of 5 volume of Optiprep (60% (wt/vol) Iodixanol, Axis-Shield PoC AS) and 1 volume of dilution medium (0.16M sucrose, 12% (wt/vol) PEG 1500, 60 mM MOPS, pH 7.4, 6 mM EDTA, 6 mM DTT, 0.6% (vol/vol) ethanol). This mixture was centrifuged at 180,000×g for 3.5 h at 4° C. in a near-vertical rotor (Beckman T pe NVT 65) using slow acceleration and deceleration modes. After centrifugation, 0.5 ml fractions were removed from the top with needle and syringe. To remove the isolation medium, the fraction material was sedimented at 17,000×g for 20 min and resuspended in PBS buffer containing 0.1% Triton X-110 and 1 mM DTT.

Marker Enzymes and Protein Content

To determine the localization in the Optiprep gradient fractions of peroxisomes, mitochondria and lysosomes, we measured activities of catalase [51], succinate dehydrogenase [52] and B-galactosidase (b-Gal Assay Kit, Invitrogen), respectively. Protein content was determined by the Bio-Rad DC protein assay reagent kit (Bio-Rad).

Polyclonal Antibodies Against Mouse Tysnd1

Rabbit polyclonal antibodies were raised against keyhole limpet hemocyanin-conjugated polypeptide SNTRDNNT-GATYPHL (SEQ ID NO: 14) corresponding to the amino acids 501-515 of Tysnd1 and affinity purified by SCRUM Inc., Tokyo. For Western blot analyses the antibodies were used at concentration 2 µg/ml. For the antibody pre-absorption assay, synthetic peptide CSNTRDNNTGATYPHL (SEQ ID NO: 15) was dissolved in Me$_2$SO at a concentration 2 mg/ml and then mixed with the primary antibody solution prior to Western blotting (40 µg peptide/5 µg antibody; about 700-fold molar excess of peptide).

Polyclonal Antibodies Against Mouse (rat) Acaa1

Rabbit polyclonal antibodies were raised against keyhole limpet homocyanin-conjugated polypeptide KLK-PAFKDGGSTTAGN (SEQ ID NO: 19) corresponding to the amino acids 259-274 of mouse Acaa1 and affinity-purified by SCRUM Inc., Tokyo. For Western blot analyses the antibodies were used at concentration 2 µg/ml.

Small Interfering RNA (siRNA)

RNA-mediated interference for down-regulating human Tysnd1 expression was done using small interfering siRNA duplexes purchased from Qiagen, Hs_Tysnd1_1_HP siRNA (siRNA Tysnd1_1) and Hs_Tysnd1_2_HP si RNA (siRNA Tysnd1_2). siRNA Tysnd1_1 targeted sequence CAG CAG AAA CCT TGC TCT GAA (SEQ ID NO: 20); siRNA Tysnd1_2 targeted sequence CCC GCT GAG CAC TTC CAT GAA (SEQ ID NO: 21). Control siRNA (Qiagen) targeted sequence AAT TCT CCG AAC GTG TCA CGT (SEQ ID NO: 22) has no homology to any known mammalian gene sequence. 293FT cells were cultured on 12-well plates. siRNA (1.2 µg) was co-transfected with 0.8 µg of either pcDNA3.1/TOPO-HA-Acaa1, pcDNA3.1/TOPO-HA-Scp2 or pcDNA3.1/TOPO-HA-Hsd17b4. The transfection was performed into 80-90% confluent cells using Lipofectamine 2000 (Invitrogen). Duplicate transfections were performed for each siRNA sample. 54 h after the start of the transfection, cells were lysed in 150 µl of SDS-PAGE sample buffer. The lysates were sonicated, incubated for 5 min at 95° C. and analyzed by Western blotting using the HA.11 monoclonal antibody (Covance).

Purification of Recombinant Tysnd1 from COS-7 Cells

COS-7 cells were transfected with cDNA3.1/TOPO-Tysnd1-FLAG using Lipofectamine 2000 transfection reagent (Invitrogen). Cells were washed 48 h post transfection with PBS and lysed with buffer A for 30 min at 4° C. with shaking. The cell lysate was centrifuged at 15,000×g for 15 min to clear the lysate of cell debris. The lysate was incubated for 90 min at 4° C. with 100 µl of anti-FLAG M2 affinity beads as per the manufacturer's protocol (Sigma). The beads were washed 4 times with buffer A and then 4 times with buffer B (50 mM HEPES, pH 8.0, 115 mM NaCl). The beads were transferred into a column and the bound protein was eluted with 300 µl of 3×FLAG peptide at 500 µg/ml in buffer B.

Cloning, Expression and Purification of the Recombinant Proteins

The coding sequences of rat Acox1, rat Acaa1 and mouse Scp2 were amplified by PCR using KOD polymerase (Toyobo). The resulting PCR products for Acox1 and Scp2 were cloned into pTrcHis2-TOPO (Invitrogen) to generate expression vectors for recombinant proteins with a C-terminal myc6×His tag. The PCR product for Acaa1 was cloned into the pQE-80L expression vector (Qiagen) to generate expression construct for Acaa1 with 6×His N-terminal tag. The expression vectors for Acox1 and Scp2 were transformed into *Escherichia coli* Top 10 cells (Invitrogen). Induction of protein expression was performed according to manufacturer's instructions. The recombinant Acox1 and Scp2 were purified from the soluble fraction of the bacterial extracts using BD TALON resin (BD Biosciences). The expression vector for Acaa1 was transformed into *Escherichia coli* BL21 Star (DE3) cells. Recombinant Acca1 was found in the insoluble fraction from which it was solubilized using 6M guanidine-HCl. Purification was performed under denaturing conditions using BD TALON resin. Refolding of the purified recombinant Acaa1 was achieved by dialysis against buffer B containing 0.5 mM DTT. The recombinant proteins were quantified using the DC Protein Assay (Bio-Rad) and spectrophotometry at 280 nm.

Assay for In Vitro Tysnd1 Processing Activity

Eight microliters of purified recombinant Tysnd1 were incubated with 6 μl of recombinant Acox1, Scp2 or Acaa1 in 50 mM Hepes, pH 8.0, 115 mM NaCl, 0.2 mM DTT at 37° C. The reaction was stopped by the addition of Laemmli sample buffer and heating for 5 min at 95° C. The reaction products were separated by 4-20% SDS-PAGE and blotted onto Hybond-P membrane. The cleavage products of recombinant Acox1 and Scp2 were detected using anti-c-Myc monoclonal antibody (Nacalai Tesque). The processing product of Acaa1 was visualized by anti-Acaa1 antibody or alternatively by staining Hybond-P membrane with 0.05% Amido Black.

N-Terminal Sequencing of the Processed Acaa1

Recombinant Acaa1 was incubated with purified Tysnd1 as described above. The processed Acaa1 was separated from the precursor form by 4-20% SDS-PAGE, blotted onto Hybond-P membrane and stained with 0.05% Amido Black. The processed 41 kDa band was excised from the membrane and underwent six cycles of the Edman degradation analysis. The sequencing analysis was performed by A. Uroshibata (Protein Group, Genomic Sciences Center, RIKEN).

N-Terminal Sequencing of the Processed Assay for In Vitro Tysnd1 Processing Activity Protease Inhibition Assay For inhibition assays, purified recombinant Tysnd1 was preincubated for 30 min at 25° C. with various protease inhibitors for 30 min. After addition of the substrate protein, the incubation proceeded for 12 h at 37° C. The following protease inhibitors were used (final concentration): pepstatin A (1 μM), EGTA (2 mM), EDTA (2 mM), 1,10-phenanthroline (1 mM), 1,7-phenanthroline (1 mM), benzamidine (1 mM), AEBSF (1 mM), aprotinin (4 μg/ml), leupeptin (10 μM), E64 (20 μM), NEM (1 mM). The processing products were assayed as described above.

Bezafibrate Treatment and Subcellular Fractionation

Six 7-week-old C57BL16J male mice were used for the experiment. The control group (n=3) was maintained on a standard diet, while experimental group (n=3) was fed with a standard diet containing 0.5% (v/w) bezafibrate. For subcellular fractionation, the livers from three animals belonging to the same group were mixed and homogenized as described above. Preparation of post-nuclear (PN) and light mitochondrial (LM) fractions was performed as described under "Purification of peroxisomes". Post-mitochondrial fraction (PM) represents a supernatant after centrifugation of PN fraction at 20,000×g for 20 min.

Results

Example 1

Tysnd1 is Targeted to the Peroxisomes

Since Tysnd1 contains a PTS1 signal, we examined whether the protein is targeted to the peroxisomes. A GFP-Tysnd1 fusion construct was co-transfected with a plasmid encoding the DsRed2-Peroxi. The full-length cDNA sequence of Tysnd1 was appended to the C-terminus of GFP to preserve PTS1 sequence at the C-terminus of the fusion protein control. The control is a fluorescent protein fused to the PTS1 signal and localizes in peroxisomes. GFP fluorescence was observed in numerous spot-like structures (FIG. 1A) but not in other parts of CHO-K1 cells. All of the GFP-Tysnd1 fusion protein-positive granules in the same sections were positive for pDsRed2-Peroxi protein (red color) (FIGS. 1B and C). This co-localization provides strong evidence that GFP-Tysnd1 has been targeted to the peroxisomes.

Example 2

Cell-Based Degradation of PTS2-Containing Peroxisomal Enzymes

A subset of peroxisomal proteins contains in their N-terminal region the PTS2 peroxisomal targeting sequence that is cleaved off once each precursor reaches its final destination [4-6]. The proteolytic enzyme(s) that cleave the PTS2 signal sequence has (have) not yet been identified. Potential candidates are the known peroxisomal proteases insulin-degrading enzyme (Ide) and peroxisome-type Lon protease and the novel peroxisomal protease Tysnd1 described in this study. Among the three proteases Tysnd1 is the most likely candidate. Ide does not work on large proteins and cleaves instead peptides less than 50 amino acids in length [53, 54], while the ATP-dependent Lon protease may function as a chaperone to degrade unfolded proteins [18].

Figure 2:
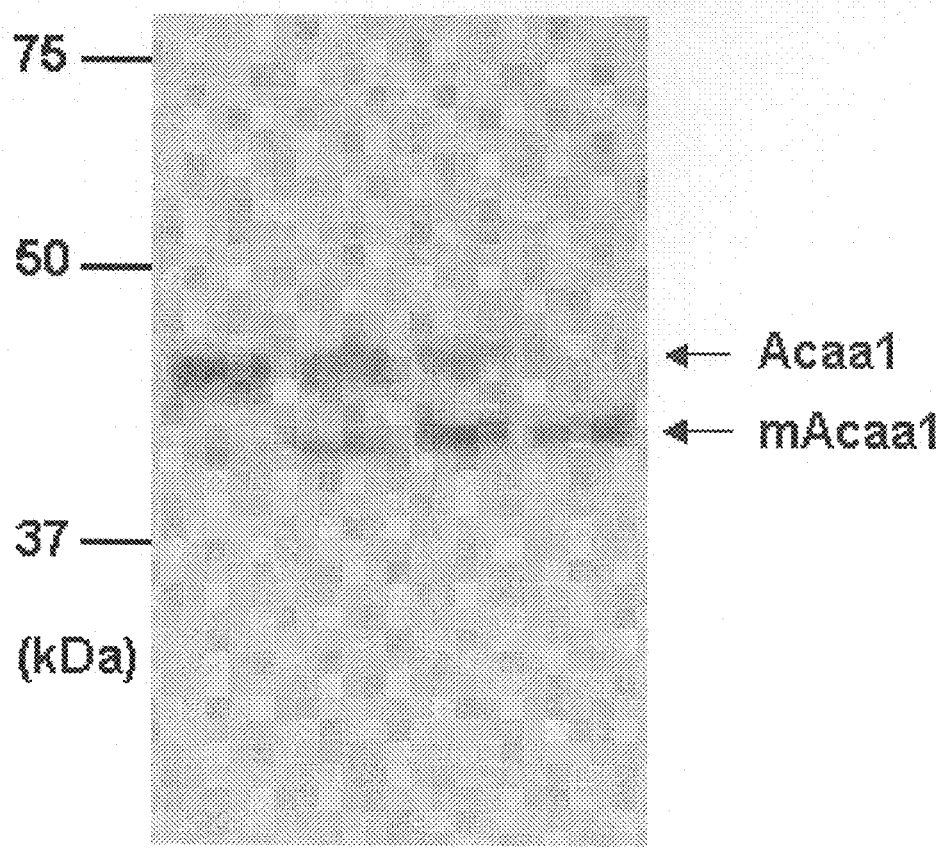
FIG. 2 shows effect of Tysnd1 expression on processing of rat Acaa1 precursor to mature Acca1 (mAcaa1). CHO-K1 cells were transiently transfected with the indicated combinations of Acaa1-HA and Tysnd1 expression plasmids. Total amounts of plasmids were kept constant at 4 µg by supplementation with the empty cDNA3.1.

To determine the role of Tysnd1 in the removal of the PTS2-containing signal sequence, we analyzed the processing of the peroxisomal 3-oxoacyl-Coenzyme A thiolase (Acaa1). Acaa1 is synthesized as a larger precursor carrying a 36-residue N-terminal removable sequence [4-6]. When the C-terminally HA-tagged Acaa1 was over-expressed in CHO cells alone, we predominately detected the unprocessed precursor form of 44 kDa. Only small quantities of HA-Acaa1 were converted to the mature 41 kDa form (FIG. 2, lane 1). Co-transfection with increasing amounts of pcDNA3.1/TOPO-FLAG-Tysnd1 led to a gradual disappearance of the 44-kDa precursor and a concurrent increase in the mature 41-kDa protein (FIG. 2, lanes 2-4). Similar results were obtained with COS-7 cells (data not shown). The results imply that Tysnd1 either represents a genuine peroxisomal processing protease that removes the PTS2-containing leader peptide or promotes the maturation of Acaa1 through the activation of a second, not yet identified peroxisomal processing protease.

Therefore Tysnd1 may be involved in the processing of all other PTS2-signal containing proteins. The physiological significance of the intra-peroxisomal processing of PTS2 proteins is not yet understood. In the case of mitochondria, the majority of precursor proteins contain cleavable amino-terminal extension sequences for mitochondrial targeting. It is believed that the removal of the signaling sequence by mitochondrial processing proteases is necessary for protein folding and further sorting within the organelle [55]. Unlike mitochondrial proteins, peroxisomal proteins are successfully translocated without prior unfolding [1]. Besides, the peroxisome matrix appears to consist of a single compartment whereas the mitochondrial space is divided into several well-defined sub-compartments. Recently Nair et al. demonstrated that PTS2 receptor Pex7p follows, like PTS1 receptor Pex5 [56], an "extended shuttle" mode of transport [57]. Pex7p enters the peroxisomes during the course of PTS2 protein import and re-emerges into the cytosol to carry out further rounds of protein import. The retention of the signal sequence of PTS2 proteins may cause these proteins to enter and leave the peroxisomes together with Pex7p, thus preventing their accumulation in the organelle.

Example 3

Processing of PTS1-Containing Peroxisomal Enzymes

In addition to PTS2 proteins, several PTS1 peroxisomal enzymes also undergo processing when translocated to the peroxisomes. These include key enzymes involved in the peroxisomal fatty acid B-oxidation, acyl-Coenzyme A oxidase 1 (Acox1), hydroxysteroid (17-beta) dehydrogenase 4 (Hsd17b4), sterol carrier protein 2 (Scp2). Therefore we investigated whether Tysnd1 can cleave rat Acox1, mouse Scp2, and mouse Hsd17b4 proteins. Acox1 consists of polypeptide components A (75 kDa), B (53 kDa) and C (22 kDa). It also exists as a hetero-oligomer comprising A2, ABC, and B2C2 [58, 59]. The B and C fragments are produced by proteolytic conversion of the A polypeptide upon translocation to the peroxisomes [60, 61]. Scp2, a protein with the molecular mass of 59 kDa is converted in the peroxisomes to 46 kDa and 13 kDa fragments [62, 63]. In the peroxisomes Scp2 is involved in the $\beta$-oxidation of acyl-CoA esters. In addition, Scp2 acts as solubilizing coprotein for $\alpha$-oxidation-dependent substrates [64].

Hsd17b4 is a bifunctional protein involved in the peroxisomal Boxidation of 2-methyl branched-chain fatty acids, C27-bile acid intermediated, very long chain fatty acids and the synthesis of poly-unsaturated fatty acids. Recently it was shown that Hsd17b4 activity is necessary for the inactivation of leukotrienes [65] and male reproductive function by maintaining lipid homeostasis in Serotoli cells of the testis [66]. Specifically, Hsd17b4 catalyzes enoyl-CoA hydratase and 3-hydroxyacyl-CoA dehydrogenase reactions in the second and third steps in peroxisomal $\beta$-oxidation of fatty acids in peroxisomes [67]. After Hsd17b4 (79 kDa) reaches peroxisomes, it is cleaved at single point to yield separate enzymatic components with the size of 35 kDa and 44 kDa.

Figure 3:
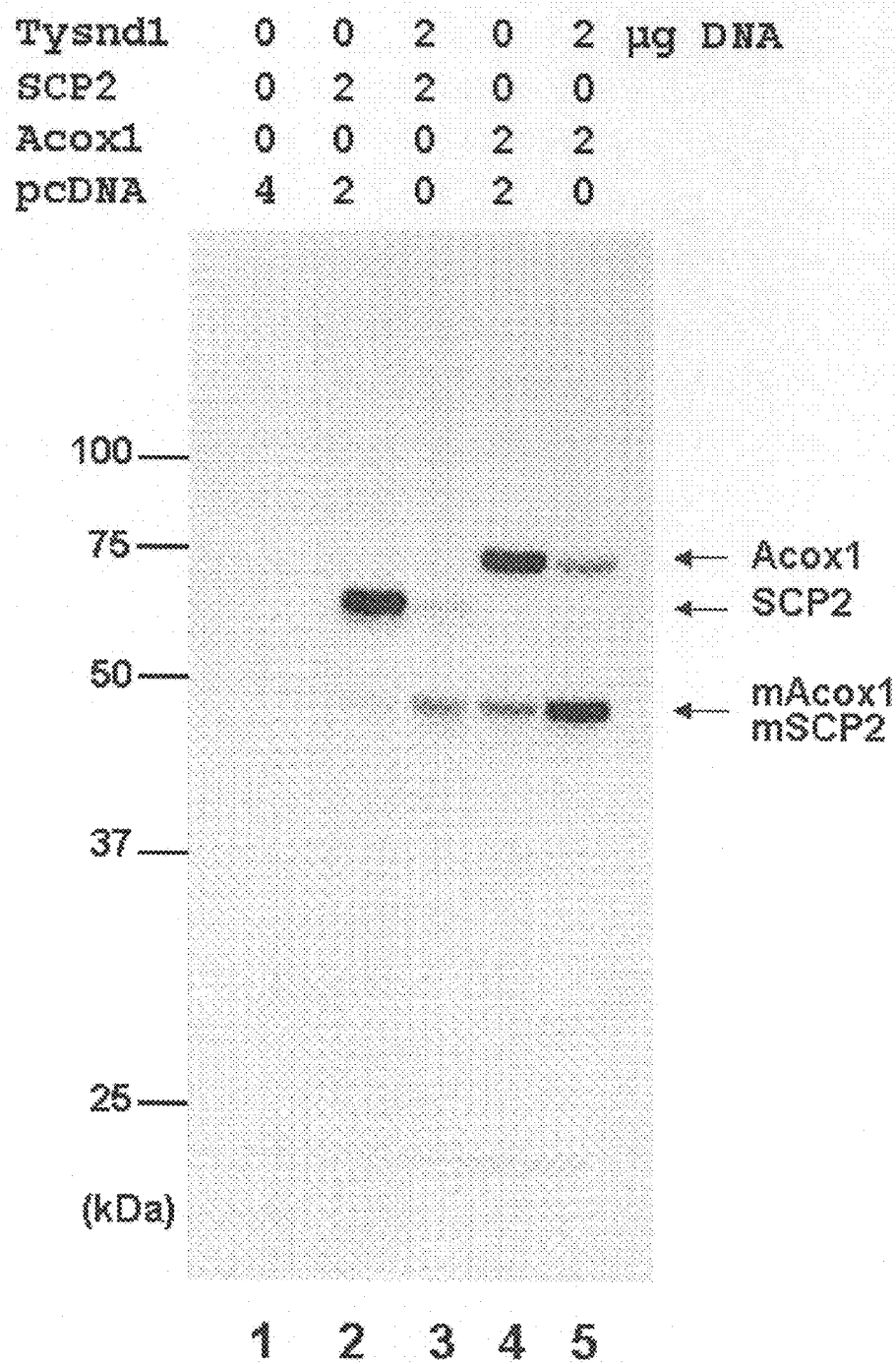
FIG. 3 shows proteolytic conversion of Scp2 and Acox1 upon co-expression of Tysnd1. COS-7 cells were transfected with the indicated combinations of FLAG-Tysnd1 and HA-mouse Scp2 or HA-rat Acox1. Total amounts of plasmids were adjusted to 4 μg using pcDNA3.1. Cell lysates were prepared 48 h after transfection, separated by 12.5% SDS-PAGE and analyzed by Western blot with the anti-HA antibody. The arrowheads indicate positions of Scp2 and Acox1 precursors and their mature forms (mScp2 and mAcox1).
Figure 4:
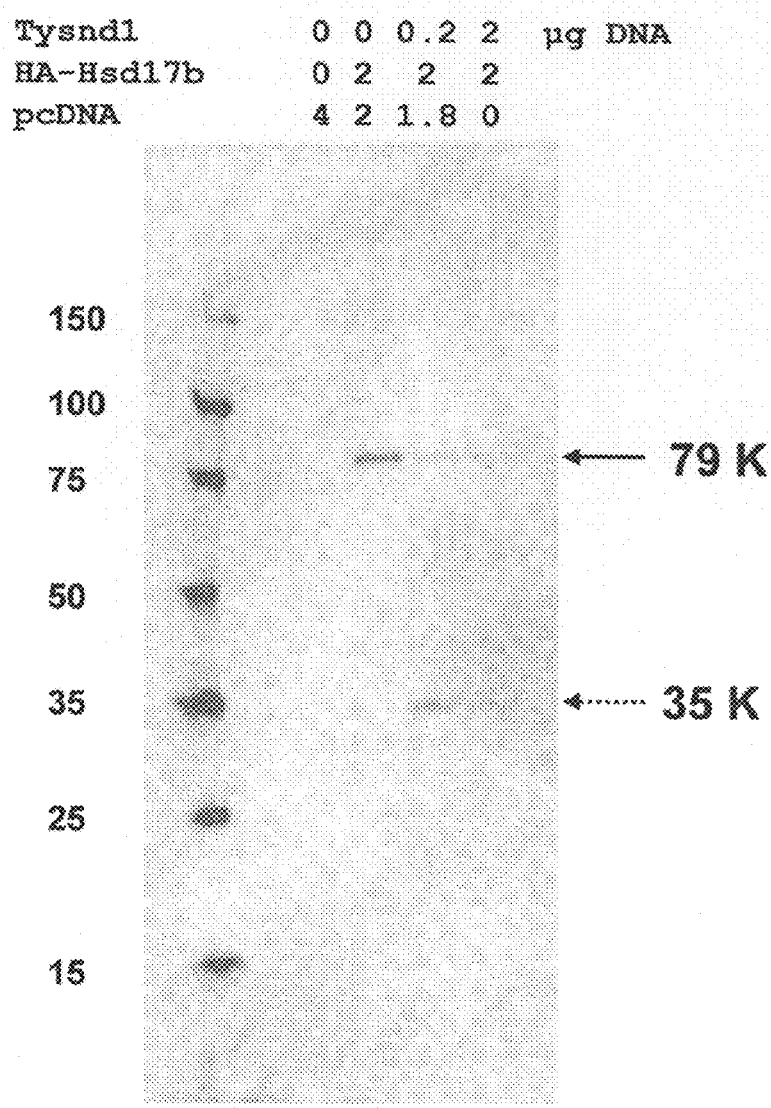
FIG. 4 shows the proteolytic conversion of mouse peroxisomal hydroxysteroid (17-beta) dehydrogenase 4 (Hsd17b4) upon co-expression of Tysnd1. COS-7 cells were transfected with the indicated combinations of FLAG-Tysnd1 and HA-mouse Hsd17b4. Total amounts of plasmids were adjusted to 4 μg using pcDNA3.1. Cell lysates were prepared 48 h after transfection and separated on a 12.5% SDS-PAGE gel and analyzed by Western blotting with the anti-HA antibody. The arrowheads indicate the positions of Hsd17b4 precursor (79 kDa) and Hsd17b4 mature form (35 kDa).

To assess the effect of Tysnd1 on proteolytic conversion of rat Acox1, mouse Scp2, and mouse Hsd17b4 the expression constructs for the proteins were transfected into COS-7 cells. Acox1, Scp2 and Hsd17b4 were tagged with a HA-epitope at their N-termini to preserve the PTS1 signal. On the Western blot Scp2 appeared mostly as a 59 kDa protein band corresponding to the unprocessed enzyme form (FIG. 3, lane 2). A very faint band of approximately 48 kDa corresponds to the processed form (FIG. 3, lane 2). Co-transfection with Tysnd1 caused significant reduction in the levels of the unprocessed 59 kDa form with a concomitant increase in the 48 kDa protein (FIG. 3, lane 3). The 13 kDa C-terminal fragment was not detected because it lacks the HA-tag. Analysis of extracts from cells transfected with HA-Acox1 revealed the presence of the predominant unprocessed 75 kDa form and the N-terminal fragment of the enzyme with an apparent size of 48 kDa (FIG. 3, lane 4). Co-expression of Tysnd1 led to a significant accumulation of the processed 48 kDa protein (FIG. 3, lane 5). Similarly HA-Hsd17b4 was processed when co-expressed with Tysnd1 to produce the N-terminal 35 kDa fragment (FIG. 4). These data clearly demonstrate that Tysnd1 is involved in cellular processing of key peroxisomal enzymes.

The proteolytic cleavage of Scp2 produces two fragments each possessing distinct activities. The 46 kDa fragment is enzymatically active as a branched-chain fatty acid thiolase [68, 69]. The 13 kDa fragment, which is also known as non-specific lipid transfer protein (nsLTP) may function in the transfer of substrates for example, fatty acyl-CoA derivatives to Acox1 [70]. The intact full-length form of the protein (59 kDa) can still perform both functions. Therefore the physiological significance of the processing is not obvious. In the case of Acox1, the role of intraperoxisomal processing is even less clear as the produced fragments remain associated. Recently, Wouters et al. [70] demonstrated that nsLTP is associated with Acox1, Acaa1 and Hsd17b4. These results suggest that the peroxisomal enzymes of the B-oxidation are organized in a functional complex [70].

The complex is thought to allow an efficient transfer of the lipid intermediates between the enzymes because of transient increase in their local concentration. We suggest that intraperoxisomal processing may lead to conformational changes of the enzymes that would enhance the formation of the complex. Tysnd1 may play a regulatory role in this process and may therefore promote an enhanced peroxisomal fatty acid $\beta$-oxidation.

Co-expression patterns of mouse genes sampled from 55 tissues [43] that are similar to the expression pattern of Tysnd1 indirectly support the proposed regulatory role. Tysnd1 (XM_125636.1), Acaa1 (XM_135249.1) and Scp2 (XM_135267.1) transcripts are co-expressed at moderate to high levels in aorta, brown fat, small intestine, liver, prostate and adrenal gland as one would expect from a protease-substrate relationship. The accession numbers are Refseq gene model accessions and were taken from reference 43.

Example 4

Posttranslational Processing of Tysnd1

Like other peroxisomal proteins, Tysnd1 is synthesized in the cytosol. To ensure that the potential Tysnd1 substrates are not processed until the import to the peroxisome is completed, the proteolytic activity of Tysnd1 should not be triggered until the protein reaches the peroxisomes. Different proteases utilize distinct strategies to silence the proteolytic activity. Most proteases are synthesized as inactive precursors and thus the key event in a proteolytic pathway is the conversion of the zymogene to the active enzyme.

To investigate the putative Tysnd1 processing, we transfected COS-7 cells with a eukaryotic expression vector for this enzyme containing a FLAG epitope either at the N- or C-terminus of the protein. It should be noted that the FLAG epitope at the C-terminus was introduced between amino acids 562 and 563 to preserve the native C-terminus of Tysnd1 which contains the PTS1 signal. Transfection with the plasmid encoding the FLAG epitope at the N-terminus of Tysnd1 resulted in the appearance of a 59 kDA protein band as determined by Western blots of cell lysates. The molecular weight is consistent with the calculated weight of the translated CDS of the cDNA sequence (FIG. 5A, lane 3). However, an additional band of approximately 10 kDa was also detected (FIG. 5A, lane 3). This small protein species corresponds to the FLAG epitope linked to approximately 90 amino acid residues at the N-terminus of Tysnd1 (FIG. 5B). On the other hand, when cells were transfected with the plasmid encoding the Flag-epitope at the C-terminus of Tysnd1, the antibodies detected an additional band of 49 kDa (FIG. 5A, lane 2). The difference in size indicates that the 10 kDa fragment is split off from the N-terminally tagged Tysnd1, thus corroborating the result obtained with the C-terminally tagged Tysnd1 protein.

In analogy to other proteases, the 59 kDa Tysnd1 protein presents the inactive precursor form that is expected to produce the catalytically active 49 kDa form. The removal of the 9 kDa N-terminal fragment does not affect two protease-related domains at residues 187 to 282 and 311 to 536. Consequently the N-terminal segment may represent an activation peptide that restrains the activity of Tysnd1 until it reaches the peroxisomes.

The conversion of the inactive precursor into the active Tysnd1 might be mediated self-catalytically or by another unidentified protease. The timing and extent of the activation event may eventually regulate the rate of peroxisomal fatty acid B-oxidation as discussed above.

Example 5

Characterization of Antibodies Against Mouse Tysnd1

Figure 5:
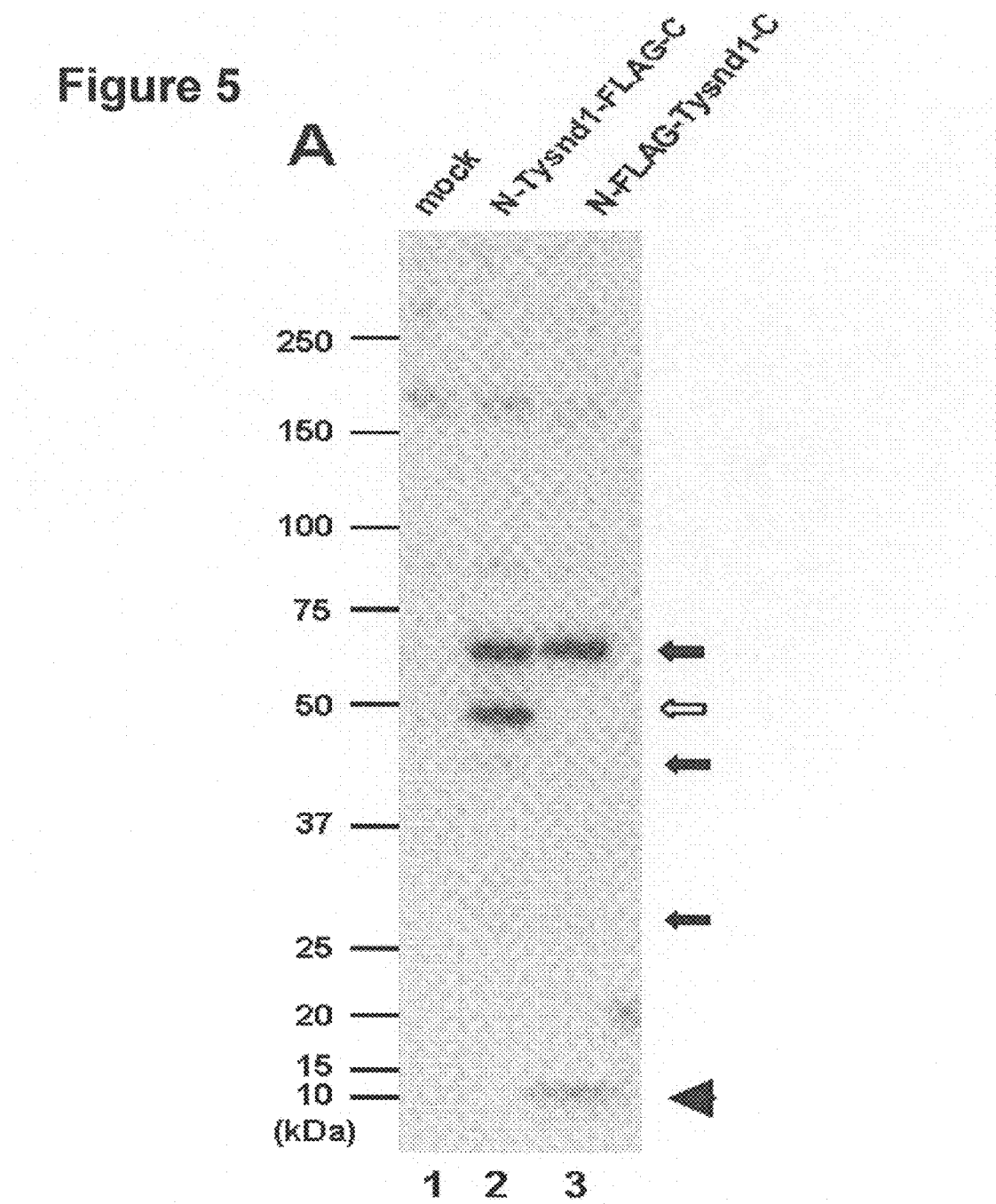
FIG. 5 shows the analysis of Tysnd1 cleavage in COS-7 cells transfected with 4 μg DNA of pcDNA3.1 (mock, lane 1), C-terminally Flag-tagged Tysnd1 (lanes 3 and 6) were resolved by 4-20% gradient SDS-PAGE and assayed by Western blotting with anti-Tysnd1 antibody. The antibody used in lanes 4-6 was preabsorbed with synthetic peptide CSN-TRDNNTGATYPHL.
Figure 5:
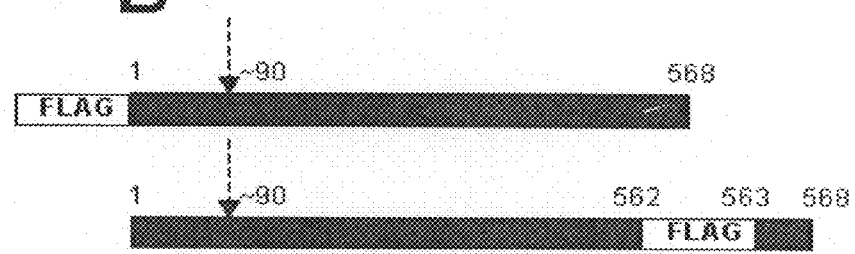
Figure 6:
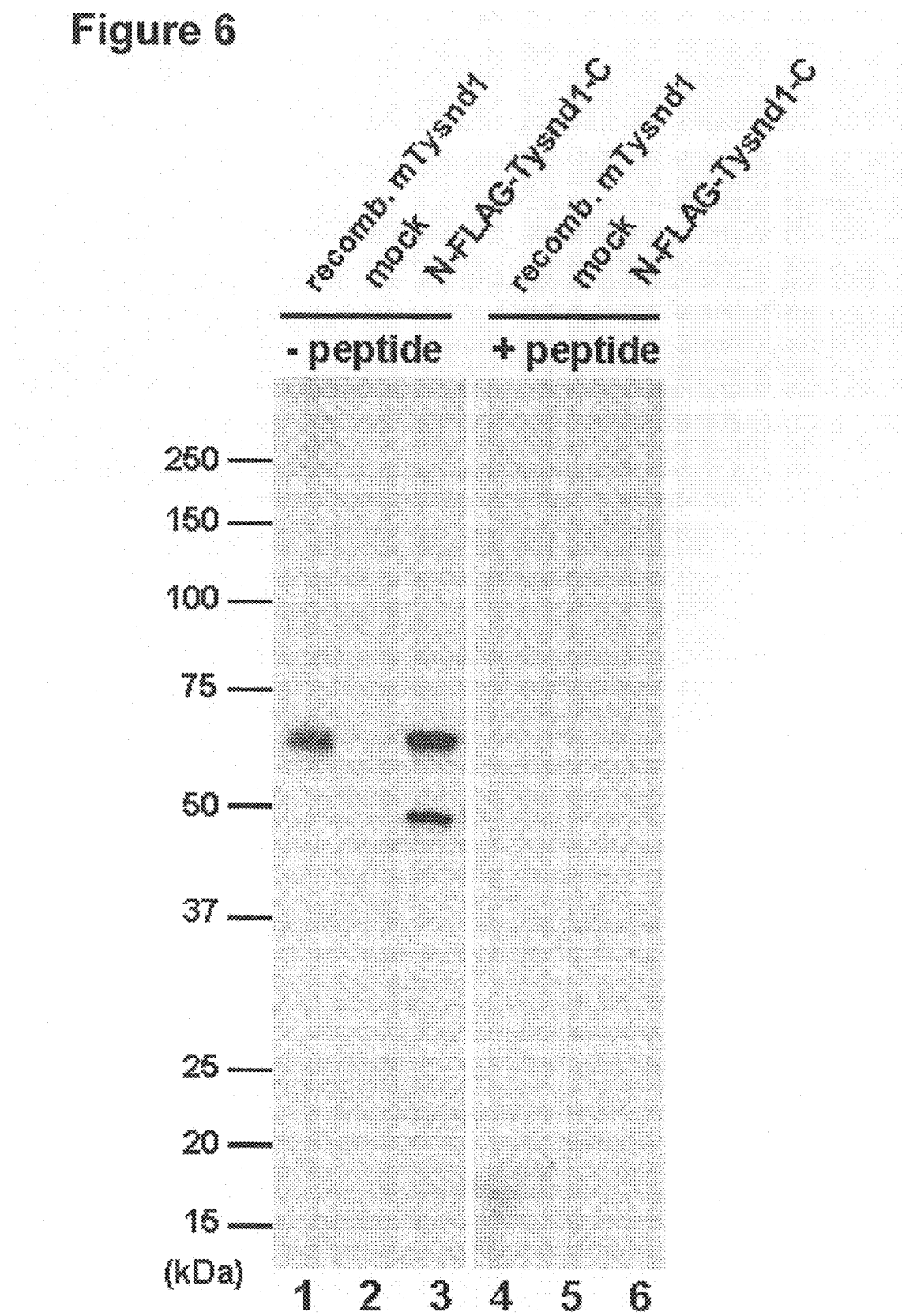
FIG. 6 shows the specific reactivity of the polyclonal antibody with Tysnd1. Purified recombinant Tysnd1 (lanes 1 and 4), lysates from COS-7 cells transfected with empty vector pcDNA3.1 (lanes 2 and 5) and transfected with a vector for N-terminally Flag-tagged Tysnd1 (lanes 3 and 6) were resolved by gradient 4-20% SDS-PAGE and assayed by Western blotting with anti-Tysnd1 antibody. The antibody used in lanes 4-6 was preabsorbed with synthetic peptide CSN-TRDNNTGATYPHL.

The rabbit polyclonal antibody was raised against a region close to the C-terminus of the mature Tysnd1 protein (amino acids 501 to 515). The specificity of the antibody was tested for its ability to recognize recombinant mouse Tysnd1 purified from E. Coli extracts and also the N-FLAG-Tysnd1-C construct in transiently transfected COS-7 cells. Western blot analysis of the recombinant Tysnd1 revealed a signal corresponding to the expected size of 59 kDa (FIG. 6, lane 1). No band could be detected in the lysates of mock-transfected COS-7 cells (FIG. 6, lane 2). Cells expressing the N-terminally Flag-tagged Tysnd1 displayed two prominent bands (FIG. 6, lane 3), The 59 kDA band fragment corresponds to Tysnd1 including the amino-terminal region. The 49 kDA fragment corresponds to the Tysnd1 protein without the amino-terminal region (see FIG. 5). To examine the specificity of the anti-Tysnd1 antibody, we performed competition assays with the synthetic peptide that was used for the immunization. The signals were completely abolished after the preabsorption of the antibody demonstrating its high specificity (FIG. 6, lanes 4-6). The sequence of the peptide used to generate the antibody against Tysnd1 (amino acids 501 to 515) is shared by rat Tysnd1 and human TYSND1, suggesting that the antibody could be also useful to study the protein expression in the tissues of these species (see below).

Example 6

Localization and Size of Endogenous Tysnd1

Figure 7:
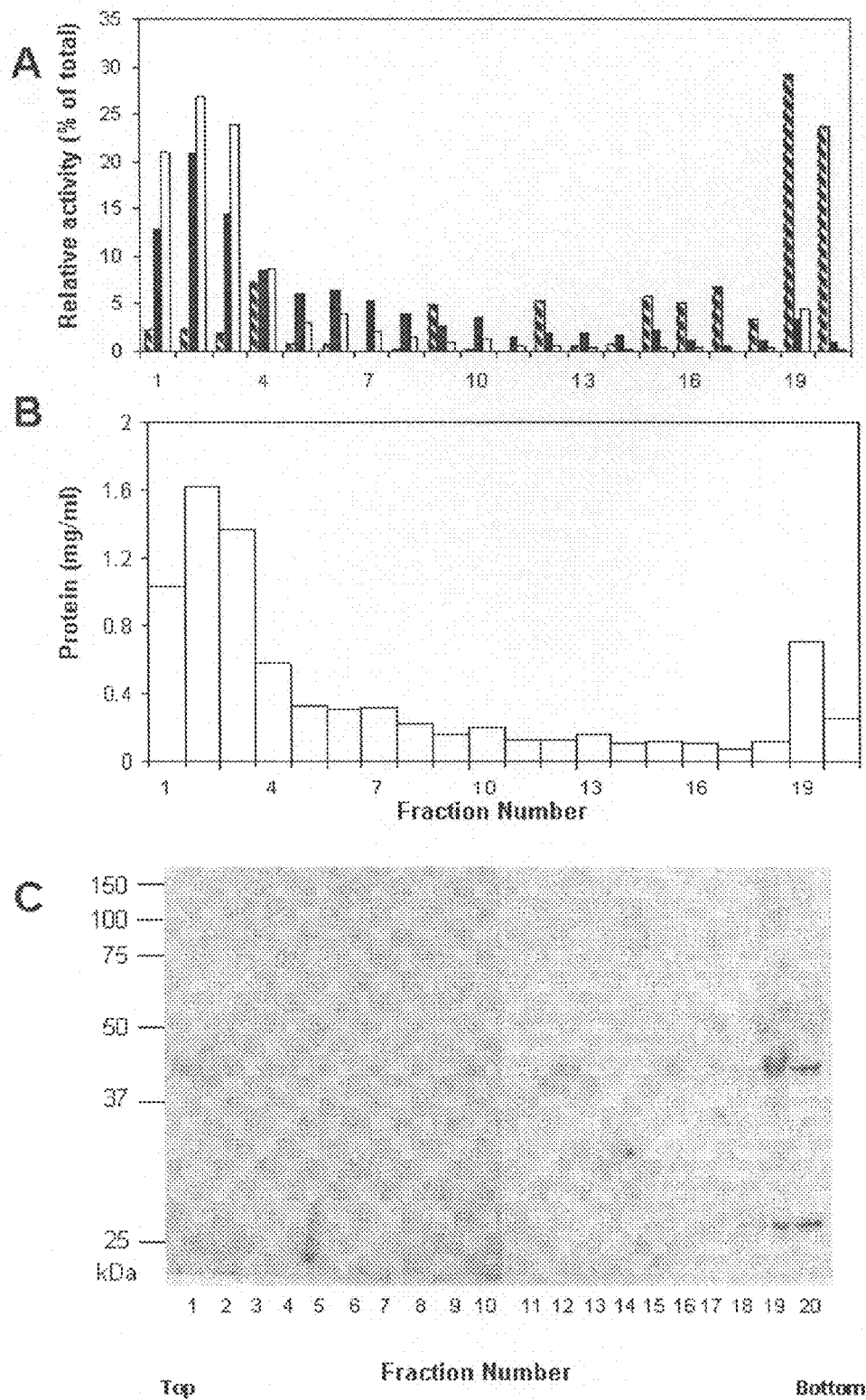
FIG. 7 shows the results of subcellular fractionation in an Optiprep density gradient. A light mitochondrial fraction was fractionated by a self-formed Optiprep gradient. The fractions were collected starting from the top of the tubes. Catalase (stripped bars), succinate dehydrogenase (filled bars) and B-galactosidase (open bars) were measured as marker enzymes for peroxisomes, mitochondria and lysosomes, respectively (FIG. 7A). Results are given as percentage of the total gradient activity.

Although the confocal microscopy experiments showed the peroxisomal localization of Tysnd1, the evidence is based on artificial conditions. For example, Tysnd1 was overexpressed as Tysnd1-GFP product in in cultured cells. Therefore we have chosen to independently confirm the peroxisomal localization of Tysnd1. We fractionated a rat liver homogenate and analyzed the subcellular fractions by immunoblotting using the anti-Tysnd1 antibody. Results of the activity of control marker enzymes (FIG. 7A) showed that peroxisomes are located near the bottom of the self-generated Optiprep gradient (fractions 18-20). The peroxisomes are well separated from the other organelles (i.e. mitochondria and lysosomes) which were found in the top fractions (fractions 1-4) and constitute the major protein content of this sample (FIG. 7B). Western blot analysis of the fractions with the anti-Tysnd1 antibody revealed immunoreactive material only in fractions 18-20 (FIG. 7C), the region of the gradient where catalase was also detected. These results strongly support the peroxisomal localization of endogenous Tysnd1. Two prominent bands detected by Western blot correspond to the protein forms with the molecular weights of 49 kDa and 27 kDa (FIG. 7C). Interestingly, in COS-7 transfected cells the major Tysnd1 species detected correspond to the intact (59 kDa) and partially processed (49 kDa) forms, while 27 kDa form is almost undetectable (FIG. 5). This is likely a consequence of the overexpression generated by the pcDNA3.1 vector, which may saturate the processing pathway of Tysnd1.

In conclusion, our data suggest that Tysnd1 may undergo a series of proteolytic events that finally lead to the formation of at least two protease forms. The first form contains both protease-related domains (49 kDa). The second one (27 kDa) contains only the C-terminal protease-like domain (308-531). Generation of separate protease domains from a single translation product in mammalian tissues is not without a precedent. Recently, Cal et al. have demonstrated that human polymerase-I [72] and polymerase-2 [73] undergo a series of proteolytic processing events that lead to the generation of three independent serine protease units. The complex nature of Tysnd1 processing appears to reflect a cellular control mechanism that enables the regulation of multiple biological processes in the peroxisomes. For example, the two forms of Tysnd1 may differ in their substrate specificity and proteolysis efficacy.

Example 7

Figure 8:
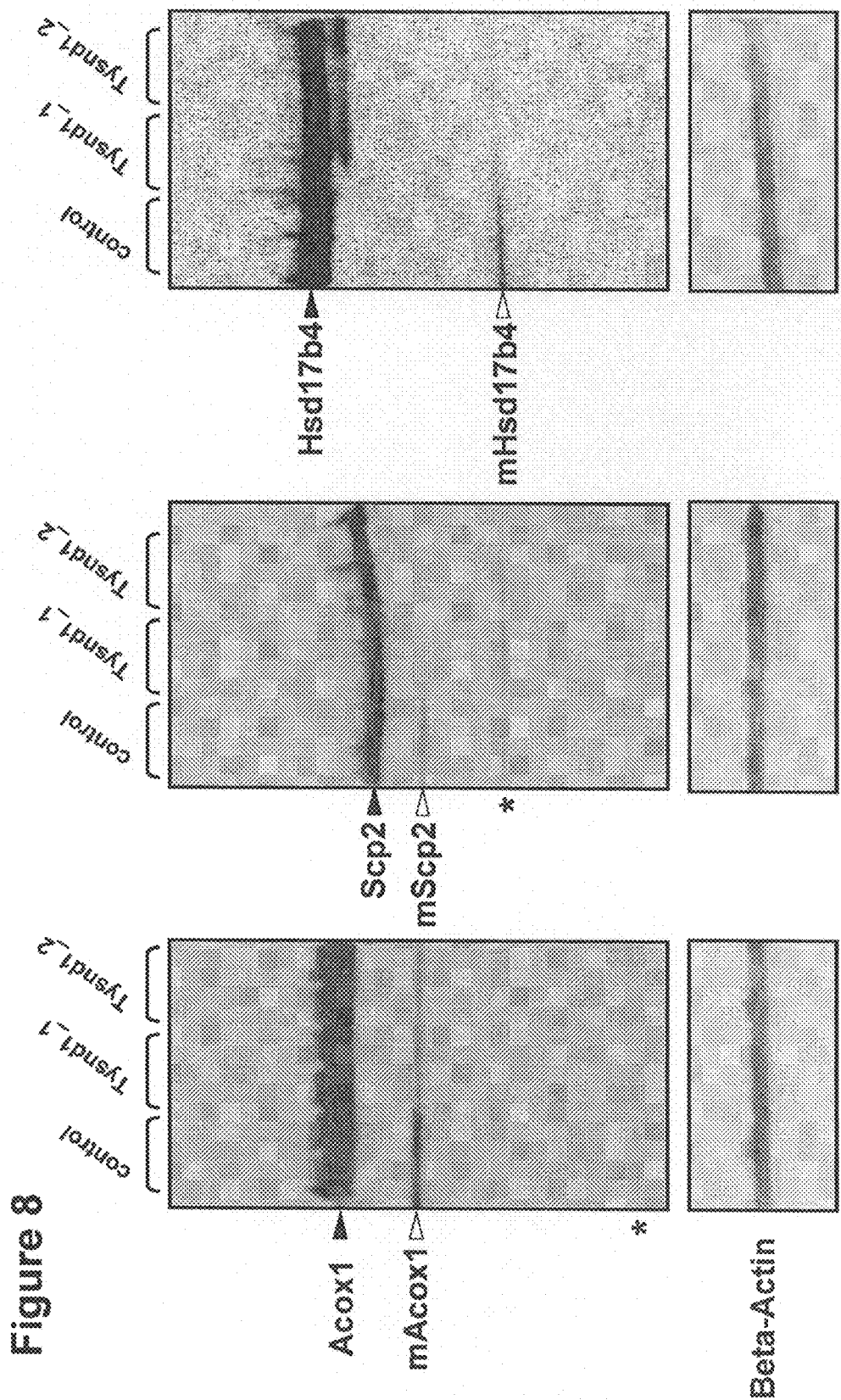
FIG. 8 shows the inhibition of Acox1, Scp2 and Hsd17b4 processing in 293FT cell line by small interfering RNA (siRNA) specific for Tysnd1. 293FT cells were transfected with Acox1-HA, Scp2-HA or Hsd17b4-HA expression plasmids together with siRNAs specific for human TYSND1 (Tysnd1_1 and Tysnd1_2 or non-silencing siRNA (control). Cell lysates were analyzed by Western blotting with the anti-HA antibody. The arrowheads indicate the positions of Acox1, Scp2 and Hsd17b4 precursors and their mature forms (mAcox1, mScp2 and mHsd17b4). Western blot analysis for beta-actin was used as a control for siRNA specificity and sample loading.

Tysnd1 is the Major Enzyme Involved in the Processing of Acox1, Scp2 and Hsd17b4 in 293FT Cells Although Tysnd1 was shown to promote cleavage of several peroxisomal enzymes in co-expression studies, the possibility remains that other proteases may also be involved in this process. We utilized small interfering RNA (siRNA) to investigate the relative contribution of Tysnd1 in the cellular processing of peroxisomal enzymes. siRNA strategies provide powerful and novel means to achieve the selective knockdown of specific proteins in cells [74]. Out of a number of mouse and human cell lines tested only 293FT cells showed detectable amounts of fragments produced from the full-length HA-Acox1, HA-Scp2 and HA-Hsd17b4 in transfection studies. The observed processing products are generated by endogenous peroxisomal processing protease present in 293FT cells. We demonstrated here that human TYSND1 specific siRNA Tysnd1__1 and Tysnd1__2 essentially blocked generation of N-terminal HA-tag containing fragments of Acox1, Scp2 and Hsd17b4 (FIG. 8). In contrast, control non-silencing siRNA was without effect (FIG. 8). Considering that siRNA may not completely knock-down the targeted mRNA and that Tysnd1 might have a long half-life time, the observed effect demonstrates that Tysnd1 plays a major if not sole role in processing of Acox1, Scp2, Hsd17b4 and possibly other peroxisomal enzymes.

Example 8

In Vitro Studies Demonstrate Direct Processing of Peroxisomal Enzymes by Tysnd1

Figure 9:
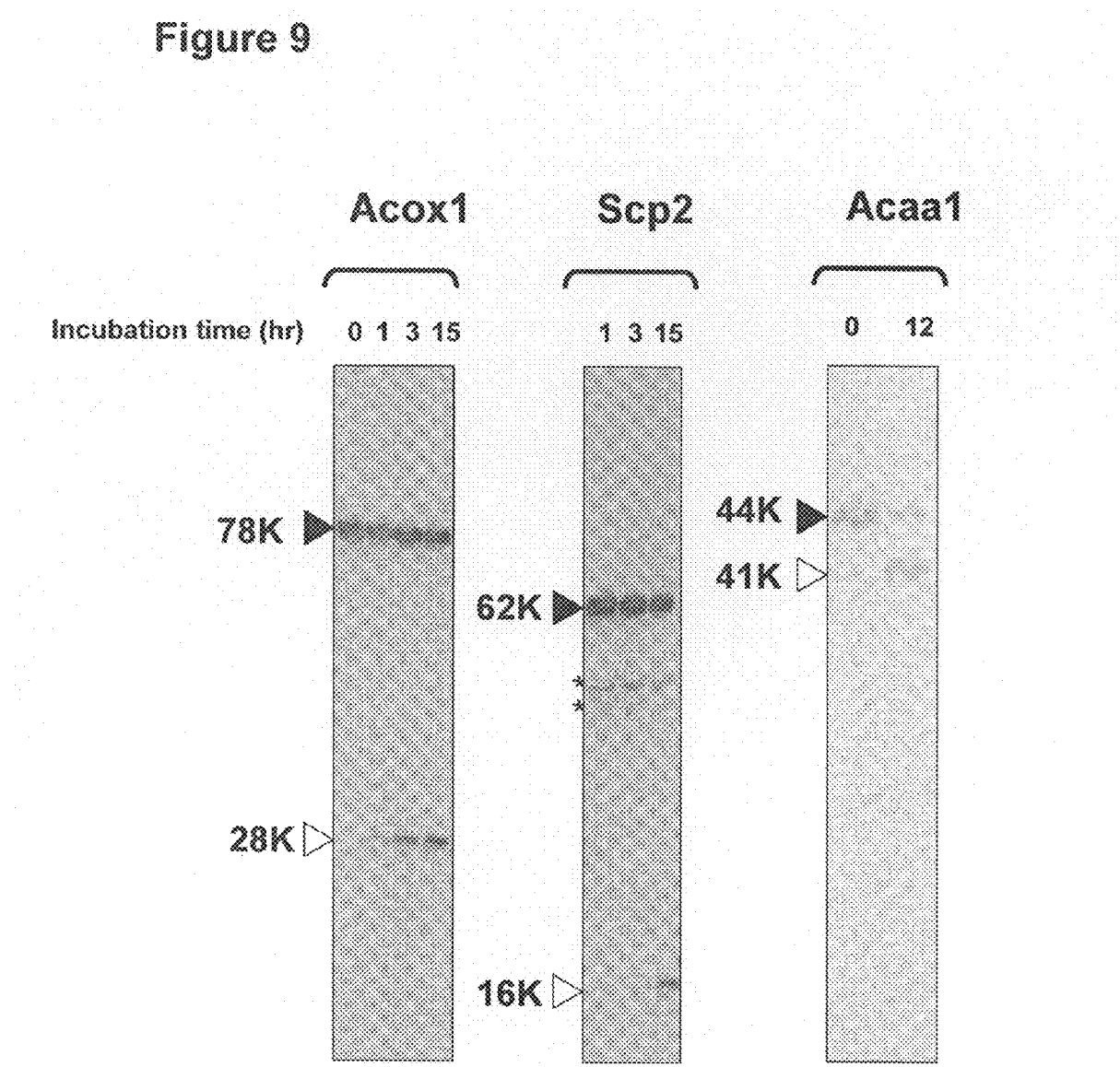
FIG. 9 shows the in vitro cleavage of Acox1, Scp2 and Acaa1 by recombinant Tysnd1. Recombinant Acox1, Scp2 and Acaa1 were purified from E. coli extracts as described in "Materials and Methods". Mouse Tysnd1 was purified from extracts of COS-7 cells transiently transfected with the Tysnd1-FLAG expression plasmid. The processing of Acox1 and Scp2 was analyzed by Western blotting with the anti-cMyc antibody. Acaa1 cleavage was detected by 0.05% Amido Black staining of the Hybond-P membrane after the transfer of the proteins from a 12.5% SDS-PAGE gel.

We have shown in a cell-based assay that Tysnd1 is involved in the processing of several peroxisomal enzymes. Tysnd1 may process its targets either directly or indirectly by activating another genuine peroxisome processing protease. To assess whether Tysnd1 directly processes peroxisomal enzymes, recombinant Tysnd1-FLAG protein was expressed in COS-7 cells and purified by affinity chromatography. Upon incubation of Tysnd1-FLAG with recombinant Acox1, Scp2 and Acaa1, cleavage products with the size identical to that generated in intact peroxisomes were formed (FIG. 9). Acox1 was cleaved to produce C-terminal fragment of 28 kDa, Scp2 was processed to generate C-terminal fragment of 16 kDa (FIG. 9). Incubation of Tysnd1 with Acaa1 resulted in the removal of 3 kDa PTS2-containing N-terminal propeptide to produce mature Acaa1 (FIG. 9). N-terminal sequence analysis established that Tysnd1 cleaves Acaa1 between residues $Cys^{26}$ and $Ser^{27}$ producing the mature form of Acaa1 found in vivo. These experiments demonstrate that Tysnd1 is a genuine peroxisomal processing protease.

The processing of peroxisomal enzymes by Tysnd1 is highly specific. Although the sequences around the cleavage sites of several peroxisomal enzymes seem to share the Ala-[AlaVal]-Pro motif [75], this is not a common rule. For example, Scp2 is cleaved in two positions which are about 25 amino acids apart. One of these sites contains the Ala-[Ala-Val]-Pro motif around the cleavage site. In Acox1 the motif was not found around the processing site. We suggest that the Tysnd1 substrate cleavage mechanism does not involve simple peptide-bond recognition but is based rather on the recognition of secondary and tertiary structures.

Example 9

Tysnd1 is a Cysteine Endopeptidase

Figure 10A:
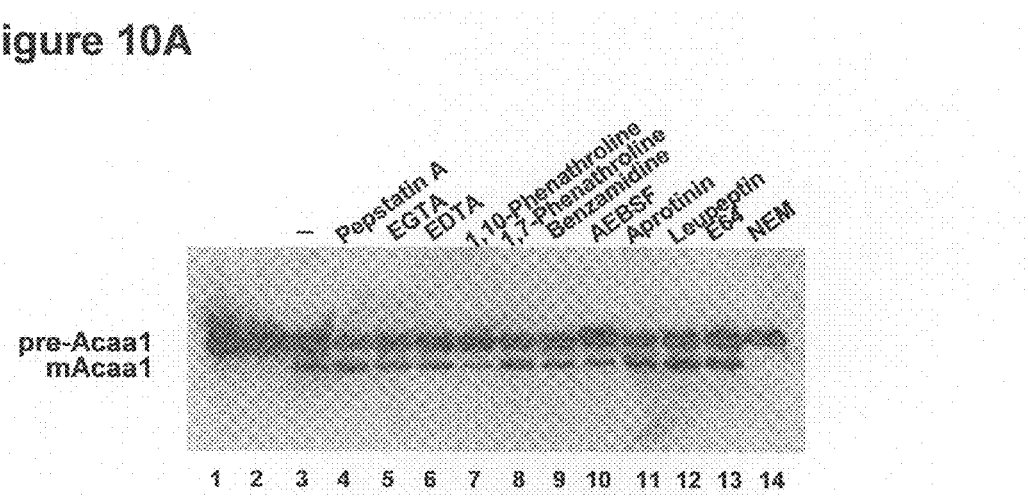
FIG. 10 shows the effect of various protease inhibitors on the processing of Acaa1 (A) and Acox1 (B) by Tysnd1. Recombinant $His_6$-Acaa1 and Acox1-myc-$His_6$ were incubated either alone for 0 (lane 1) or 12 h (lane 2) or with Tysnd1-FLAG purified from COS-7 cell lysates for 12 h (A, lanes 3-14; B, lanes 3-17). Processing of $His_6$-Acaa1 was assessed by Western blot with the anti-Acaa1 antibody. The cleavage of Acox1-myc-$His_6$ was detected using the anti-cMyc antibody.
Figure 10B:
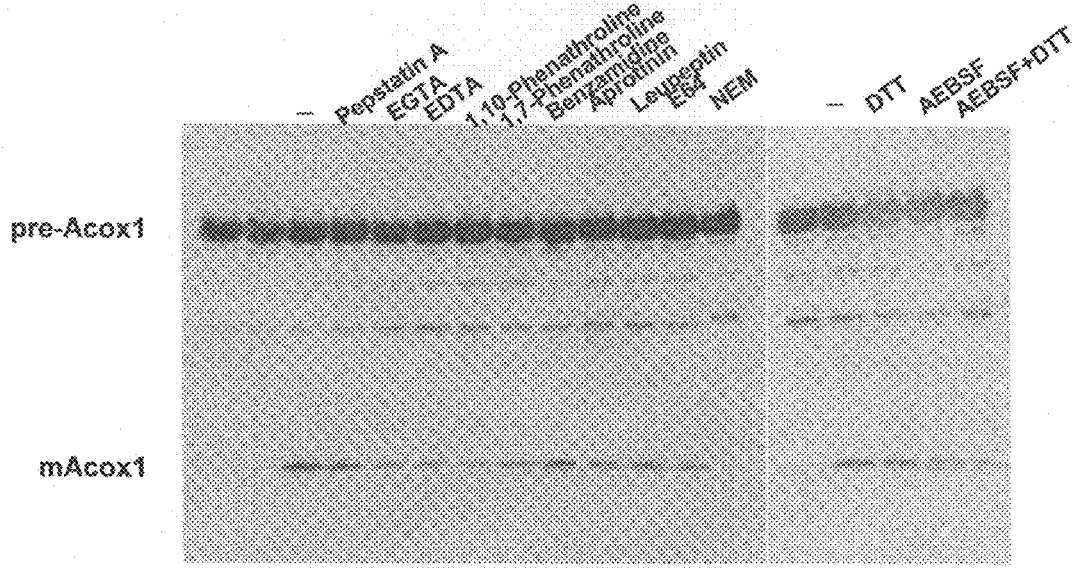

In order to determine the protease class of Tysnd1 the enzyme-processing activity was assessed in the presence of various protease inhibitors. Two substrates were selected for this experiment: Acaa1 and Acox1. In addition to being representatives of different peroxisome targeting classes (PTS1 and PTS2), Acaa1 and Acox1 differ in the amino acid sequence surrounding the processing sites. The Tysnd1 processing activity was completely abolished with the cysteine protease inhibitor N-ethylmaleimide (NEM) (Sigma)(FIG. 10). Although Tysnd1 is susceptible to the sulfhydryl-active agent NEM, it is resistant to two other cysteine proteinase inhibitors, leupeptin and trans-epoxysuccinyl-1-leucylamido-(4-guanidino) butane (E64)(Peptide Institute Inc. (Osaka, Japan). Leupeptin is known to inhibit some lysosomal serine and cysteine proteases, while E64 is a specific inhibitor of the papain protease family [76]. A similar inhibition pattern was observed for the peroxisomal protease IDE, which is inhibited by NEM but not by leupeptin and E64. Partial inhibition of Tysnd1 by metal chelators (FIG. 10) notably by 1,10-phenanthroline (Sigma) but not by related, non-chelating compound 1,7-phenanthroline (Wako Pure Chemical Industries) indicates that Zn ions might be involved in the stabilization of Tysnd1 conformation or complex formation with its substrates.

Example 10

Induction of Tysnd1 by Hypolipidemic Drug Bezafibrate

Figure 11:
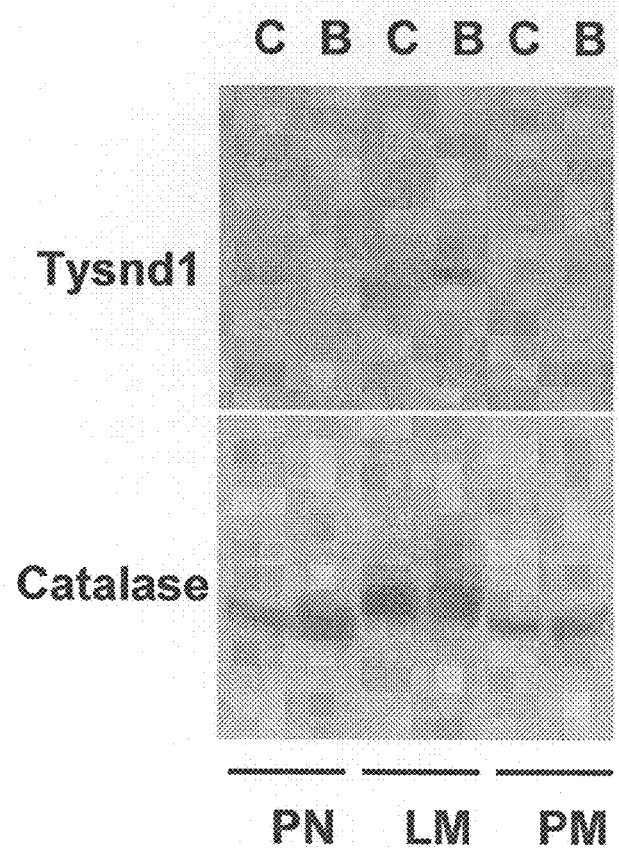
FIG. 11 shows the effect of bezafibrate treatment on the content of Tysnd1 in mouse liver. Mice were maintained for 3 weeks on a standard diet containing 0.5% (v/w) bezafibrate. Liver subcellular fractions were prepared as described for rat liver under "Materials and Methods". One hundred μg of protein of post-nuclear (PN), light mitochondrial (LM) and post-mitochondrial (PM) was analyzed by Western blot with the anti-Tysnd1 antibody or anti-catalase antibody. C, control mice; B, bezafibrate-treated mice samples.

The PPAR-α-activator bezafibrate is known to increase liver B-oxidation of fatty acids, in part due to the induction of responsible peroxisomal enzymes Acaa1, Acox1 and Hsd17b4 [77] which are processed by Tysnd1. We therefore tested whether Tysnd1 is also induced by bezafibrate. In agreement with previous reports, we observed the induction of the liver Acox1, Hsd17b4, and Acaa1 mRNA (not shown). Subcellular fractionation of the liver was performed to assess the content of Tysnd1 protein. Treatment with bezafibrate led to a significant increase in the 49 kDa form of Tysnd1 in the light mitochondrial fraction enriched in peroxisomes (FIG. 11). In contrast, we observed only a slight increase in the total quantity of catalase and no increase in the enzyme content in the light mitochondrial FIG. 11). These data suggest that the expression of Tysnd1 might be co-regulated with the expression of its substrate proteins to meet the metabolic needs, particularly in conditions of enhanced B-oxidation of fatty acids.

Example 11

Implications of Tysnd1 PTS1 and PTS2 Protein Processing Activity for Diseases

The processing of Acox1, Acaa1, Scp2, Hsd17b4 and possibly other PTS2 and PTS1-containing peroxisomal proteins by Tysnd1 may have potential therapeutic or diagnostic implications on the pathogenesis of fatty acid β-oxidation, ketogenesis and cholesterol synthesis in metabolic diseases such as dietary obesity, fatty liver disease or hypercholesterolemia. The association of Tysnd1 with fat metabolism and its differential expression in microvascular endothelial cells [78, Table 6 of this reference] may also imply a role of Tysnd1 dysfunctions in the pathogenesis of cardiovascular diseases. During heart ischemia the high rates of mitochondrial fatty acid oxidation rates inhibit glucose oxidation [79]. It was shown that ranolazine and the long-chain 3-ketoacyl-Coenzyme A thiolase inhibitor trimetazidine inhibit fatty acid oxidation and therefore increase glucose oxidation and cardiac efficiency [80]. Although the peroxisomal thiolase contribution to heart ischemia has to our knowledge not been investigated, it cannot be excluded. Inhibition of Tysnd1 may reduce the availability of thiolase and thereby decreasing fatty acid oxidation while increasing cardiac efficiency.

Studies on the long-term effect of high-fat diet in mice have demonstrated that the expression of Acox1, Acaa1 in liver is significantly up-regulated [81, 82]. Specific inhibition or activation of mature Tysnd1 may therefore open up new strategies for controlling pathophysiological hepatic lipid metabolism and male fertility [66]. Lack of mature Scp2 in mouse is implicated in the accumulation of phytanic acid and the development of adult Refsum disease-like syndromes [83]. Phytanic acid is degraded by phytanoyl-CoA 2-hydroxylase in the peroxisomal α-oxidation pathway. Since the efficient 2-hydroxylation of phythanoyl-CoA by phytanoyl-CoA 2-hydroxylase requires mature Scp2, Tysnd1 may play an important role regulating the availability of mature Scp2. Functional defects in Tysnd1 may therefore result in Refsum-like disease symptoms.

A study by Raychaudhury et al. [84] showed that *Leishmania* infection results in multiple functional deficiencies of peroxisomal enzymes that lead to peroxisomal damage. Of note is that the authors also detected a decrease in peroxisomal proteolytic activity upon *Leishmania* infection. The activity decrease upon infection might be caused by *Leishmania* proteins that inhibit the mature Tysnd1 protease activity or the conversion of Tysnd1 precursor to mature Tysnd1.

REFERENCES

1. Subramani S, Koller A, Snyder W B. Import of peroxisomal matrix and membrane proteins. Annu Rev Biochem. 2000; 69:399-418.
2. Purdue P E, Lazarow P B. Peroxisome biogenesis. Annu Rev Cell Dev Biol. 2001; 17:701-52.
3. Olivier L M, Kovacs W, Masuda K, Keller G A, Krisans S K. Identification of peroxisomal targeting signals in cholesterol biosynthetic enzymes. AA-CoA thiolase, hmg-coa synthase, MPPD, and FPP synthase. J Lipid Res. 2000 December; 41(12):1921-35.
4. Osumi T, Tsukamoto T, Hata S, Yokota S, Miura S, Fujiki Y, Hijikata M, Miyazawa S, Hashimoto T. Amino-terminal presequence of the precursor of peroxisomal 3-ketoacyl-CoA thiolase is a cleavable signal peptide for peroxisomal targeting. Biochem Biophys Res Commun. 1991 Dec. 31; 181(3):947-54.

5. Swinkels B W, Gould S J, Bodnar A G, Rachubinski R A, Subramani S. A novel, cleavable peroxisomal targeting signal at the amino-terminus of the rat 3-ketoacyl-CoA thiolase. EMBO J. 1991 November; 10(11):3255-62.
6. Tsukamoto T, Hata S, Yokota S, Miura S, Fujiki Y, Hijikata M, Miyazawa S, Hashimoto T, Osumi T. Characterization of the signal peptide at the amino terminus of the rat peroxisomal 3-ketoacyl-CoA thiolase precursor. J Biol. Chem. 1994 Feb. 25; 269(8):6001-10.
7. Hettema E H, Distel B, Tabak H F. Import of proteins into peroxisomes. Biochim Biophys Acta. 1999 Aug. 12; 1451 (1):17-34.
8. Titorenko V I, Rachubinski R A. The life cycle of the peroxisome. Nat Rev Mol Cell Biol. 2001 May; 2(5):357-68.
9. Titorenko V I, Rachubinski R A. The peroxisome: orchestrating important developmental decisions from inside the cell. J. Cell Biol. 2004 Mar. 1; 164(5):641-5.
10. Cohen G B, Rangan V S, Chen B K, Smith S, Baltimore D. The human thioesterase II protein binds to a site on HIV-1 Nef critical for CD4 down-regulation. J Biol. Chem. 2000 Jul. 28; 275(30):23097-105.
11. Gavva N R, Wen S C, Daftari P, Moniwa M, Yang W M, Yang-Feng L P, Seto E, Davie J R, Shen C K. NAPP2, a peroxisomal membrane protein, is also a transcriptional corepressor. Genomics. 2002 March; 79(3):423-31.
12. van der Klei I J, Veenhuis M. Yeast peroxisomes: function and biogenesis of a versatile cell organelle. Trends Microbiol. 1997 December; 5(12):502-9.
13. Veenhuis M, Kiel J A, Van Der Klei I J. Peroxisome assembly in yeast. Microsc Res Tech. 2003 Jun. 1; 61(2): 139-50.
14. Olsen L J. The surprising complexity of peroxisome biogenesis. Plant Mol. Biol. 1998 September; 38(1-2):163-89.
15. Hannaert V, Michels P A. Structure, function, and biogenesis of glycosomes in kinetoplastida. J Bioenerg Biomembr. 1994 April; 26(2):205-12.
16. Moyersoen J, Choe J, Fan E, Hol W G, Michels P A. Biogenesis of peroxisomes and glycosomes: trypanosomatid glycosome assembly is a promising new drug target. FEMS Microbiol Rev. 2004 November; 28(5):603-43.
17. van de Kamp M, Driessen A J, Konings W N. Compartmentalization and transport in beta-lactam antibiotic biosynthesis by filamentous fungi. Antonie Van Leeuwenhoek. 1999 January-February; 75(1-2):41-78.
18. Kikuchi M, Hatano N, Yokota S, Shimozawa N, Imanaka T, Taniguchi H. Proteomic analysis of rat liver peroxisome: presence of peroxisome-specific isozyme of Lon protease. J Biol. Chem. 2004 Jan. 2; 279(1):421-8.
19. Gould S J, Valle D. Peroxisome biogenesis disorders: genetics and cell biology. Trends Genet. 2000 August; 16(8):340-5.
20. Jansen G A, Waterham H R, Wanders R J. Molecular basis of Refsum disease: sequence variations in phytanoyl-CoA hydroxylase (PHYH) and the PTS2 receptor (PEX7). Hum Mutat. 2004 March; 23(3):209-18.
21. Sacksteder K A, Gould S J. The genetics of peroxisome biogenesis. Annu Rev Genet. 2000; 34:623-652.
22. Titorenko V I, Smith J J, Szilard R K, Rachubinski R A. Pex20p of the yeast *Yarrowia lipolytica* is required for the oligomerization of thiolase in the cytosol and for its targeting to the peroxisome. J. Cell Biol. 1998 Jul. 27; 142(2): 403-20.
23. Glover J R, Andrews D W, Rachubinski R A. *Saccharomyces cerevisiae* peroxisomal thiolase is imported as a dimer. Proc Natl Acad Sci USA. 1994 Oct. 25; 91(22):10541-5.
24. Leiper J M, Oatey P B, Danpure C J. Inhibition of alanine: glyoxylate aminotransferase 1 dimerization is a prerequisite for its peroxisome-to-mitochondrion mistargeting in primary hyperoxaluria type 1. J. Cell Biol. 1996 November; 135(4):939-51.
25. Bellion E, Goodman J M. Proton ionophores prevent assembly of a peroxisomal protein. Cell. 1987 Jan. 16; 48(1):165-73.
26. Waterham H R, Russell K A, Vries Y, Cregg J M. Peroxisomal targeting, import, and assembly of alcohol oxidase in *Pichia pastoris*. J. Cell Biol. 1997 Dec. 15; 139(6):1419-31.
27. Marzioch M, Erdmann R, Veenhuis M, Kunau W H. PAS7 encodes a novel yeast member of the WD-40 protein family essential for import of 3-oxoacyl-CoA thiolase, a PTS2-containing protein, into peroxisomes. EMBO J. 1994 Oct. 17; 13(20):4908-18.
28. Albertini M, Rehling P, Erdmann R, Girzalsky W. Kiel J A, Veenhuis M, Kunau W H. Pex14p, a peroxisomal membrane protein binding both receptors of the two PTS-dependent import pathways. Cell. 1997 Apr. 4; 89(1):83-92.
29. Elgersma Y, Elgersma-Hooisma M, Wenzel T, McCaffery J M, Farquhar M G, Subramani S. A mobile PTS2 receptor for peroxisomal protein import in *Pichia pastoris*. J. Cell Biol. 1998 Feb. 23; 140(4):807-20.
30. Szilard R K, Titorenko V I, Veenhuis M, Rachubinski R A. Pay32p of the yeast *Yarrowia lipolytica* is an intraperoxisomal component of the matrix protein translocation machinery. J. Cell Biol. 1995 December; 131(6 Pt 1):1453-69.
31. Zhang J W, Lazarow P B. PEB1 (PAS7) in *Saccharomyces cerevisiae* encodes a hydrophilic, intra-peroxisomal protein that is a member of the WD repeat family and is essential for the import of thiolase into peroxisomes. J. Cell Biol. 1995 April; 129(1):65-80.
32. Morita M, Kurochkin I V, Motojima K, Goto S, Takano T, Okamura S, Sato R, Yokota S, Imanaka T. Insulin-degrading enzyme exists inside of rat liver peroxisomes and degrades oxidized proteins. Cell Struct Funct. 2000 October; 25(5):309-15.
33. Kurochkin I V, RIKEN GER Group, GSL Members, Konagaya A, Nagashima T, Schönbach C. Identification of Potential Peroxisomal Proteins in Mouse. Genome Res. 2003 June; 13(6b):1560. [http://www.genome.org/cgi/content/full/13/6b/1560]
34. Kurochkin I V, Schönbach C. Konagaya A. In Silico Prediction of Peroxisomal Proteins in Mouse. Genome Informatics 2003 December; 14:539-40 [http://www.jsbi.org/journal/GIWO3/GIW03P068.pdf]
35. Kurochkin I V, Nagashima T, Konagaya A, Schönbach C. Sequence-based Discovery of the Human and Rodent Peroxisomal Proteome. Appl Bioinformatics; in press June 2005.
36. UCSC Genome browser; mouse Tysnd1 http://genome.ucsc.edu/cgi-bin/hgacks?db=mm5&position=chr10:61457382-61464 634&hgsid=39784308
37. UCSC Genome browser; human TYSND1 http://genome.ucsc.edu/cgi-bin/hgTracks?db=hg17&position=chr10:71568974-71575 956&hgsid=39784308
38. Gene Entrez mouse Tysnd1 http://www.ncbi.nlm.nih.gov/entrez/query.fcgi?db=gene&cmd=Retrieve&dopt=Graphics&list_uids=71767
39. Gene Entrez human TYSND1 http://www.ncbi.nlm.nih.gov/entrez/query.fcgi?db=gene&cmd=Retrieve&dopt=Graphics&list_uds=219743
40. Swissprot/TrEMBL mouse Tysnd1 and human TYSND1 http://kr.expasy.org/cgi-bin/sprot-search-de?TYSND1

41. InterPro domain: Peptidase, trypsin-like serine and cysteine proteases http://www.ebi.ac.uk/interpro/ISpy?mode=single&ac=[SwissProt/TrEMBL accession number]
42. UCSC Genome browser; gene expression for mouse Tysnd1 and neighbors http://genome.ucsc.edu/cgi-bin/hgNear?hgsid=39784308&org=Mouse&db=mm5&near_search=AK005069&submit=Go%21&near.order=expGnfAtlas2&near.count=50
43. Mouse Gene Prediction Database; Search Results for 1300019N10Rik (XM_125636.1) and top 100 correlated genes; http://mgpd.med.utoronto.ca/profile.php?nameofgene=XM_125636.1
44. UCSC Genome browser; gene expression for human TYSND1 and neighbors http://genome.ucsc.edu/cgi-bin/hgNear?hgsid=73232388&org=Human&db=hg18&near_search=TYSND1&submit=Go%21&near_order=expGnfAtlas2&near.count=50
45. Array Prospector gene expression for human TYSND1 (SwissProt/TrEBML accession Q96AR5) http://string.embl-heidelberg.de:8080/prophecies cgi/new_prophecies/new_prophecies.pl?genename=Q96AR5&species=9606&colorcode=1&maxgenes=10&submit=SUB MIT
46. Kawai J, et al., RIKEN Genome Exploration Research Group Phase II Team and the FANTOM Consortium.Functional annotation of a full-length mouse cDNA collection. Nature. 2001 Feb. 8; 409(6821):685-90.
47. Okazaki Y et al., FANTOM Consortium; RIKEN Genome Exploration Research Group Phase, I & II Team. Analysis of the mouse transcriptome based on functional annotation of 60,770 full-length cDNAs. Nature. 2002 Dec. 5; 420 (6915):563-73.
48. Van Veldhoven P P, Baumgart E, Mannaerts G P. Iodixanol (Optiprep), an improved density gradient medium for the iso-osmotic isolation of rat liver peroxisomes. Anal Biochem. 1996 May 15; 237(1):17-23.
49. McClelland G B, Khanna S, Gonzalez G F, Butz C E, Brooks G A. Peroxisomal membrane monocarboxylate transporters: evidence for a redox shuttle system? Biochem Biophys Res Commun. 2003 Apr. 25; 304(1):130-5.
50. Antonenkov V D, Sormunen R T, Hiltunen J K. The behavior of peroxisomes in vitro: mammalian peroxisomes are osmotically sensitive particles. Am J Physiol Cell Physiol. 2004 December; 287(6):C1623-35.
51. Johansson L H, Borg L A. A spectrophotometric method for determination of catalase activity in small tissue samples. Anal Biochem. 1988 October; 174(1):331-6.
52. Pennington R J. Biochemistry of dystrophic muscle. Mitochondrial succinate-tetrazolium reductase and adenosine triphosphatase. Biochem J. 1961 September; 80:649-54.
53. Duckworth, W. C., Bennett, R. G. & Hamel, F. G. (1998) Insulin degradation: progress and potential. Endocr Rev. 1998 October; 19(5):608-24.
54. Kurochkin, I. V. (2001) Insulin-degrading enzyme: embarking on amyloid destruction. Trends Biochem Sci. 2001 July; 26(7):421-5
55. Gakh O, Cavadini P, Isaya G. Mitochondrial processing peptidases. Biochim BiophysActa. 2002 Sep. 2; 1592(1):63-77.
56. Dammai V, Subramani S. The human peroxisomal targeting signal receptor, Pex5p, is translocated into the peroxisomal matrix and recycled to the cytosol. Cell. 2001 Apr. 20; 105(2):187-96.
57. Nair D M, Purdue P E, Lazarow P B. Pex7p translocates in and out of peroxisomes in *Saccharomyces cerevisiae*. J. Cell Biol. 2004 Nov. 22; 167(4):599-604.
58. Tsukamoto T, Yokota S, Fujiki Y. Isolation and characterization of Chinese hamster ovary cell mutants defective in assembly of peroxisomes. J. Cell Biol. 1990 March; 110 (3):651-60.
59. Miyazawa S, Hayashi H, Hijikata M, Ishii N, Furuta S, Kagamiyama H, Osumi T, Hashimoto T. Complete nucleotide sequence of cDNA and predicted amino acid sequence of rat acyl-CoA oxidase. J Biol. Chem. 1987 Jun. 15; 262(17):8131-7.
60. Miyazawa S, Osumi T, Hashimoto T, Ohno K, Miura S, Fujiki Y Peroxisome targeting signal of rat liver acyl-coenzyme A oxidase resides at the carboxy terminus. Mol Cell Biol. 1989 January; 9(1):83-91.
61. Wirtz K W. Phospholipid transfer proteins revisited. Biochem J. 1997 Jun. 1; 324 (Pt 2):353-60.
62. Seedorf U, Ellinghaus P, Roch Nofer J. Sterol carrier protein-2. Biochim Biophys Acta. 2000 Jun. 26; 1486(1):45-54.
63. Otera H, Nishimura M, Setoguchi K, Mori T, Fujiki Y. Biogenesis of nonspecific lipid transfer protein and sterol carrier protein x: studies using peroxisome assembly-defective pex cell mutants. J Biol. Chem. 2001 Jan. 26; 276 (4):2858-64.
64. Mukherji M, Kershaw N J, Schofield C J, Wierzbicki A S, Lloyd M D. Utilization of sterol carrier protein-2 by phytanoyl-CoA 2-hydroxylase in the peroxisomal alpha oxidation of phytanic acid. Chem. Biol. 2002 May; 9(5): 597-605.
65. Ferdinandusse S, Denis S, Van Roermund C W, Wanders R J, Dacremont G. Identification of the peroxisomal beta-oxidation enzymes involved in the degradation of long-chain dicarboxylic acids. J Lipid Res. 2004 June; 45(6): 1104-11.
66. Huyghe S, Schmalbruch H, De Gendt K, Verhoeven G, Guillou F. Van Veldhoven P P, Baes M. Peroxisomal multifunctional protein 2 is essential for lipid homeostasis in Sertoli cells and male fertility in mice. Endocrinology. 2006 Feb. 16; [Epub ahead of print as doi:10.1210/en.2005-1571]
67. Jiang L L, Kurosawa T, Sato M, Suzuki Y, Hashimoto T. Physiological role of D-3-hydroxyacyl-CoA dehydratase/D-3-hydroxyacyl-CoA dehydrogenase bifunctional protein. J Biochem (Tokyo). 1997 March; 121(3):506-13.
68. Seedorf U, Brysch P. Engel T, Schrage K, Assmann G. Sterol carrier protein X is peroxisomal 3-oxoacyl coenzyme A thiolase with intrinsic sterol carrier and lipid transfer activity. J Biol. Chem. 1994 Aug. 19; 269(33):21277-83.
69. Antonenkov V D, Van Veldhoven P P, Waelkens E, Mannaerts G P. Substrate specificities of 3-oxoacyl-CoA thiolase A and sterol carrier protein 2/3-oxoacyl-CoA thiolase purified from normal rat liver peroxisomes. Sterol carrier protein 2/3-oxoacyl-CoA thiolase is involved in the metabolism of 2-methyl-branched fatty acids and bile acid intermediates. J Biol. Chem. 1997 Oct. 10; 272(41):26023-31.
70. Wouters F S, Bastiaens P I, Wirtz K W, Jovin T M. FRET microscopy demonstrates molecular association of non-specific lipid transfer protein (nsL-TP) with fatty acid oxidation enzymes in peroxisomes. EMBO J. 1998 Dec. 15; 17(24):7179-89.
71. InterPro domain view for mouse Tysnd1 http://www.ebi.ac.uk/interpro/ISpy?mode=single&ac=Q9DBA6
72. Cal S, Quesada V, Garabaya C, Lopez-Otin C. Polyserase-I, a human polyprotease with the ability to generate independent serine protease domains from a single translation product. Proc Natl Acad Sci USA. 2003 Aug. 5; 100(16): 9185-90.
73. Cal S, Quesada V, Llamazares M, Diaz-Perales A, Garabaya C, Lopez-Otin C. Human polymerase-2, a novel enzyme with three tandem serine protease domains in a single polypeptide chain. J Biol. Chem. 2005 Jan. 21; 280 (3):1953-61.
74. Sandy P, Ventura A, Jacks T. Mammalian RNAi: a practical guide. Biotechniques. 2005 August; 39(2):215-24.
75. Biermann J, van den Bosch H. In vitro processing of the human alkyl-dihydroxyacetonephosphate synthase precursor. Arch Biochem Biophys. 1999 Aug. 1; 368(1):139-46.
75. Salvesen G S, Nagase H. In *Proteolytic Enzymes* (ed. Beynon R and Bond J S), p. 110. Oxford University Press.
77. Beier K, Volkl A, Hashimoto T, Fahimi H D. Selective induction of peroxisomal enzymes by the hypolipidemic drug bezafibrate. Detection of modulations by automatic image analysis in conjunction with immunoelectron microscopy and immunoblotting. Eur J. Cell Biol. 1988 August; 46(3):383-93.
78. Keen H L, Ryan M J, Beyer A, Mathur S, Scheetz T E, Gackle B D, Faraci F M, Casavant T L, Sigmund C D. Gene expression profiling of potential PPARgamma target genes in mouse aorta. Physiol Genomics. 2004 Jun. 17; 18(1):33-42.
79. Dyck J R, Cheng J F, Stanley W C, Barr R, Chandler M P, Brown S, Wallace D, Arrhenius T, Harmon C, Yang G, Nadzan A M, Lopaschuk G D. Malonyl coenzyme a decarboxylase inhibition protects the ischemic heart by inhibiting fatty acid oxidation and stimulating glucose oxidation. Circ Res. 2004 May 14; 94(9):e78-84.
80. Lopaschuk G D. Inhibiting fatty acid oxidation as a novel therapeutic approach to treating, ischaemic heart disease. Cardiovasc J S Afr. 2004 July; 15(4 Suppl 1):S1.
81. Murase, T., Mizuno, T., Omachi, T., Onizawa, K., Komine, Y., Kondo, H., Hase, T., Tokimitsu, I., 2001. Dietary diacylglycerol suppresses high fat and high sucrose diet-induced body fat accumulation in C57BL/6J mice. J. Lipid Res. 42, 372-378.
82. Kim S, Sohn I, Ahn J I, Lee K H, Lee Y S, Lee Y S. Hepatic gene expression profiles in a long-term high-fat diet-induced obesity mouse model. Gene. 2004 Sep. 29; 340(1): 99-109.
83. Mukherji M, Kershaw N J, Schofield C J, Wierzbicki A S, Lloyd M D. Utilization of sterol carrier protein-2 by phytanoyl-CoA 2-hydroxylase in the peroxisomal alpha oxidation of phytanic acid. Chem. Biol. 2002 May; 9(5): 597-605.
84. Raychaudhury B, Banerjee S, Datta S C. Peroxisomal function is altered during *leishmania* infection. Med Sci Monit. 2003 April; 9(4):BR125-9

What is claimed is:

1. A method for screening for an agent that can modulate Tysnd1 levels in a cell, comprising steps of:
   contacting an animal cell with a candidate substance;
   estimating an amount of Tysnd1 in the cell;
   identifying the candidate substance as the agent if the amount of Tysnd1 is modulated with respect to a control.

2. A method according to claim 1, wherein the amount of Tysnd1 increases.

3. A method according to claim 1, wherein the amount of Tysnd1 decreases.

4. A method according to claim 1, wherein the agent is capable of inducing the expression of Tysnd1.

5. A method according to claim 1, wherein the agent is capable of inhibiting the expression of Tysnd1.

6. A method for screening for an agent that can modulate Tysnd1 activity in a cell, comprising the steps of:
   contacting an animal cell with a candidate substance;
   measuring Tysnd1 activity in said cell;
   and identifying the candidate substance as the agent if the activity of Tysnd1 in the cell is modulated with respect to a control.

* * * * *

SEQUENCE LISTING

```
<160> NUMBER OF SEQ ID NOS: 22

<210> SEQ ID NO 1
<211> LENGTH: 25
<212> TYPE: DNA
<213> ORGANISM: Artificial
<220> FEATURE:
<223> OTHER INFORMATION: B1 (forward primer)

<400> SEQUENCE: 1
ggatccatgg ggcggcaatg gggac                                           25

<210> SEQ ID NO 2
<211> LENGTH: 27
<212> TYPE: DNA
<213> ORGANISM: Artificial
<220> FEATURE:
<223> OTHER INFORMATION: B2 (reverse primer)

<400> SEQUENCE: 2
ggatcctcag agcttgctcc gtgggac                                         27

<210> SEQ ID NO 3
<211> LENGTH: 58
<212> TYPE: DNA
<213> ORGANISM: Artificial
<220> FEATURE:
<223> OTHER INFORMATION: AX1 (forward primer)

<400> SEQUENCE: 3
accatgggct acccttacga cgtgcctgac tacgccaacc ccgacctgcg caaggagc       58

<210> SEQ ID NO 4
<211> LENGTH: 25
<212> TYPE: DNA
<213> ORGANISM: Artificial
<220> FEATURE:
<223> OTHER INFORMATION: AX2 (reverse primer)

<400> SEQUENCE: 4
```

```
tcaaagcttg gactgcaggg gcttc                                          25

<210> SEQ ID NO 5
<211> LENGTH: 59
<212> TYPE: DNA
<213> ORGANISM: Artificial
<220> FEATURE:
<223> OTHER INFORMATION: S5 (forward primer)

<400> SEQUENCE: 5
accatgggct acccttacga cgtgcctgac tacgcccctt ctgtcgcttt gaaatctcc    59

<210> SEQ ID NO 6
<211> LENGTH: 21
<212> TYPE: DNA
<213> ORGANISM: Artificial
<220> FEATURE:
<223> OTHER INFORMATION: S2 (reverse primer)

<400> SEQUENCE: 6
ctcctcacag cttagctttg c                                              21

<210> SEQ ID NO 7
<211> LENGTH: 48
<212> TYPE: DNA
<213> ORGANISM: Artificial
<220> FEATURE:
<223> OTHER INFORMATION: FN (forward primer)

<400> SEQUENCE: 7
ccaccatgga ctacaaagac gatgacgaca agggcggca atggggac                  48

<210> SEQ ID NO 8
<211> LENGTH: 24
<212> TYPE: DNA
<213> ORGANISM: Artificial
<220> FEATURE:
<223> OTHER INFORMATION: FLAG epitope

<400> SEQUENCE: 8
gactacaaag acgatgacga caag                                           24

<210> SEQ ID NO 9
<211> LENGTH: 16
<212> TYPE: DNA
<213> ORGANISM: Artificial
<220> FEATURE:
<223> OTHER INFORMATION: Tysnd1 sequence positions

<400> SEQUENCE: 9
gggcggcaat ggggac                                                    16

<210> SEQ ID NO 10
<211> LENGTH: 24
<212> TYPE: DNA
<213> ORGANISM: Artificial
<220> FEATURE:
<223> OTHER INFORMATION: FC1 (forward primer)

<400> SEQUENCE: 10
ccaccatggg gcggcaatgg ggac                                           24

<210> SEQ ID NO 11
<211> LENGTH: 66
<212> TYPE: DNA
```

```
<213> ORGANISM: Artificial
<220> FEATURE:
<223> OTHER INFORMATION: FC2 (reverse primer)

<400> SEQUENCE: 11
tcagagcttg ctccgtggga ccttgtcgtc atcgtctttg tagtcttcgg acaggggccg    60
ctgcag                                                               66

<210> SEQ ID NO 12
<211> LENGTH: 24
<212> TYPE: DNA
<213> ORGANISM: Artificial
<220> FEATURE:
<223> OTHER INFORMATION: FLAG epitope

<400> SEQUENCE: 12
cttgtcgtca tcgtctttgt agtc                                           24

<210> SEQ ID NO 13
<211> LENGTH: 6
<212> TYPE: PRT
<213> ORGANISM: Homo sapiens

<400> SEQUENCE: 13

Val Pro Arg Ser Lys Leu
1               5

<210> SEQ ID NO 14
<211> LENGTH: 15
<212> TYPE: PRT
<213> ORGANISM: Mus musculus

<400> SEQUENCE: 14

Ser Asn Thr Arg Asp Asn Asn Thr Gly Ala Thr Tyr Pro His Leu
1               5                   10                  15

<210> SEQ ID NO 15
<211> LENGTH: 16
<212> TYPE: PRT
<213> ORGANISM: Artificial
<220> FEATURE:
<223> OTHER INFORMATION: synthetic peptide

<400> SEQUENCE: 15

Cys Ser Asn Thr Arg Asp Asn Asn Thr Gly Ala Thr Tyr Pro His Leu
1               5                   10                  15

<210> SEQ ID NO 16
<211> LENGTH: 7
<212> TYPE: PRT
<213> ORGANISM: Artificial
<220> FEATURE:
<223> OTHER INFORMATION: HA-tag peptide

<400> SEQUENCE: 16

Tyr Asp Val Pro Asp Tyr Ala
1               5

<210> SEQ ID NO 17
<211> LENGTH: 57
<212> TYPE: DNA
<213> ORGANISM: Artificial
<220> FEATURE:
<223> OTHER INFORMATION: Hsd17b4-Fwd (forward)

<400> SEQUENCE: 17
```

```
accatgggct acccttacga cgtgcctgac tacgccgctt cgccgctgag gttcgac        57

<210> SEQ ID NO 18
<211> LENGTH: 27
<212> TYPE: DNA
<213> ORGANISM: Artificial
<220> FEATURE:
<223> OTHER INFORMATION: Hsd17b4-Rev (reverse)

<400> SEQUENCE: 18
tcagagcttg gcatagtctt taagaat                                        27

<210> SEQ ID NO 19
<211> LENGTH: 16
<212> TYPE: PRT
<213> ORGANISM: Mus musculus

<400> SEQUENCE: 19

Lys Leu Lys Pro Ala Phe Lys Asp Gly Gly Ser Thr Thr Ala Gly Asn
1               5                   10                  15

<210> SEQ ID NO 20
<211> LENGTH: 21
<212> TYPE: DNA
<213> ORGANISM: Artificial
<220> FEATURE:
<223> OTHER INFORMATION: siRNA Tysnd1_1 targeted sequence

<400> SEQUENCE: 20
cagcagaaac cttgctctga a                                              21

<210> SEQ ID NO 21
<211> LENGTH: 21
<212> TYPE: DNA
<213> ORGANISM: Artificial
<220> FEATURE:
<223> OTHER INFORMATION: siRNA Tysnd1_2 targeted sequence

<400> SEQUENCE: 21
cccgctgagc acttccatga a                                              21

<210> SEQ ID NO 22
<211> LENGTH: 21
<212> TYPE: DNA
<213> ORGANISM: Artificial
<220> FEATURE:
<223> OTHER INFORMATION: Control siRNA targeted sequence

<400> SEQUENCE: 22
aattctccga acgtgtcacg t                                              21
```